US008246968B2

(12) United States Patent
Zale et al.

(10) Patent No.: US 8,246,968 B2
(45) Date of Patent: *Aug. 21, 2012

(54) CANCER CELL TARGETING USING NANOPARTICLES

(75) Inventors: Stephen E. Zale, Hopkinton, MA (US); Mir Mukkaram Ali, Woburn, MA (US)

(73) Assignee: Bind Biosciences, Inc., Cambridge, MA (US)

( * ) Notice: Subject to any disclaimer, the term of this patent is extended or adjusted under 35 U.S.C. 154(b) by 163 days.

This patent is subject to a terminal disclaimer.

(21) Appl. No.: 12/059,496

(22) Filed: Mar. 31, 2008

(65) Prior Publication Data
US 2009/0061010 A1 Mar. 5, 2009

Related U.S. Application Data

(60) Provisional application No. 60/976,197, filed on Sep. 28, 2007.

(51) Int. Cl.
A61K 9/00 (2006.01)
A61K 9/51 (2006.01)
A61K 31/74 (2006.01)
A61K 9/14 (2006.01)
C07C 229/00 (2006.01)

(52) U.S. Cl. ........ 424/400; 977/904; 977/905; 977/906; 977/911; 977/915; 514/588; 514/674; 560/34; 562/439

(58) Field of Classification Search .......................... None
See application file for complete search history.

(56) References Cited

U.S. PATENT DOCUMENTS

| 5,543,158 | A | 8/1996 | Gref et al. |
| 5,578,325 | A | 11/1996 | Domb et al. |
| 6,007,845 | A | 12/1999 | Domb et al. |
| 6,139,870 | A | 10/2000 | Verrecchia |
| 6,254,890 | B1 | 7/2001 | Hirosue et al. |
| 6,265,609 | B1 | 7/2001 | Jackson et al. |
| 6,395,718 | B1 | 5/2002 | Slusher et al. |
| 6,528,499 | B1 | 3/2003 | Kozikowski et al. |
| 6,841,547 | B2* | 1/2005 | Brown et al. ............... 514/152 |
| 6,875,886 | B2 | 4/2005 | Frangioni |
| 6,902,743 | B1 | 6/2005 | Setterstrom et al. |
| 7,422,902 | B1 | 9/2008 | Wheeler et al. |
| 2002/0119916 | A1 | 8/2002 | Hassan |
| 2003/0143184 | A1 | 7/2003 | Seo et al. |
| 2004/0054190 | A1 | 3/2004 | Pomper et al. |
| 2004/0086544 | A1 | 5/2004 | Bezemer et al. |
| 2004/0247680 | A1 | 12/2004 | Farokhzad et al. |
| 2005/0037075 | A1 | 2/2005 | Farokhzad et al. |
| 2005/0136258 | A1 | 6/2005 | Nie et al. |
| 2005/0256071 | A1 | 11/2005 | Davis |
| 2006/0002852 | A1 | 1/2006 | Saltzman et al. |
| 2006/0002971 | A1 | 1/2006 | Saltzman et al. |
| 2006/0057219 | A1 | 3/2006 | Nagasaki et al. |
| 2006/0110460 | A1 | 5/2006 | Ferret et al. |
| 2006/0165987 | A1 | 7/2006 | Hildgen et al. |
| 2007/0041901 | A1 | 2/2007 | Diener et al. |
| 2007/0043066 | A1 | 2/2007 | Sum et al. |
| 2007/0053845 | A1 | 3/2007 | Sengupta et al. |
| 2008/0057102 | A1 | 3/2008 | Roorda |
| 2008/0081074 | A1 | 4/2008 | Gu et al. |
| 2008/0124400 | A1 | 5/2008 | Liggins et al. |
| 2008/0193381 | A1* | 8/2008 | Babich et al. .................. 424/9.1 |
| 2009/0061010 | A1 | 3/2009 | Zale et al. |
| 2009/0074828 | A1 | 3/2009 | Alexis et al. |
| 2010/0068285 | A1 | 3/2010 | Zale et al. |
| 2010/0068286 | A1 | 3/2010 | Troiano et al. |
| 2010/0069426 | A1 | 3/2010 | Zale et al. |
| 2010/0104655 | A1 | 4/2010 | Zale et al. |
| 2010/0216804 | A1 | 8/2010 | Zale et al. |
| 2010/0226986 | A1 | 9/2010 | Grayson et al. |

FOREIGN PATENT DOCUMENTS

| EP | 2106806 | 10/2009 |
| KR | 10-0418916 | 3/2002 |
| KR | 20020041712 | 6/2004 |
| WO | WO-/2005/046572 | 5/2005 |
| WO | WO-/2006/093991 | 9/2006 |
| WO | WO-2007/034479 | 3/2007 |
| WO | WO-/2007/133807 | 11/2007 |
| WO | WO /2008/019142 | 2/2008 |
| WO | WO-2008/058192 | 5/2008 |

(Continued)

OTHER PUBLICATIONS

Farokhzad, Omid C.; Cheng, Jianjun; Teply, Benjamin A.; Sherifi, Ines; Jon, Sangyong; Kantoff, Philip W.; Richie, Jerome P.; and Langer, Robert; "Targeted nanoparticle-aptamer bioconjugates for cancer chemotherapy in vivo," 2006, The National Academy of Sciences; PNAS, vol. 103, No. 16, p. 6315-6320.*

Farokhzad, Omid C.; Cheng, Jianjun; Teply, Benjamin A.; Sheriff, Ines; Jon, Sangyong; Kantoff, Philip W.; Richie, Jerome P.; and Langer, Robert; "Targeted nanoparticle-aptamer bioconjugates for cancer chemotherapy in vivo," 2006, The National Academy of Sciences; PNAS, vol. 103, No. 16, p. 6315-6320.*

Sapra, P. et al.; "Ligand-targeted liposomal anticancer drugs", 2003, Pergamon, Progress in Lipid Research, vol. 42, pp. 439-462.*

Gao, Xiaohu et al.; "In vivo cancer targeting and imaging with semiconductor quantum dots", 2004, Nature Publishing Group, Nature Biotechnology, vol. 22, No. 8, pp. 969-976.*

(Continued)

Primary Examiner — David J Blanchard
Assistant Examiner — Ivan Greene
(74) Attorney, Agent, or Firm — Darlene A. Vanstone, Esq.; Carolyn S. Elmore, Esq.; Elmore Patent Law Group, PC

(57) ABSTRACT

The present invention generally relates to polymers and macromolecules, in particular, to polymers useful in particles such as nanoparticles. One aspect of the invention is directed to a method of developing nanoparticles with desired properties. In one set of embodiments, the method includes producing libraries of nanoparticles having highly controlled properties, which can be formed by mixing together two or more macromolecules in different ratios. One or more of the macromolecules may be a polymeric conjugate of a moiety to a biocompatible polymer. In some cases, the nanoparticle may contain a drug. Other aspects of the invention are directed to methods using nanoparticle libraries.

4 Claims, 4 Drawing Sheets

FOREIGN PATENT DOCUMENTS

| WO | WO-/2008/105773 | 9/2008 |
|---|---|---|
| WO | WO-2008/121949 | 10/2008 |
| WO | WO-/2008/124632 | 10/2008 |
| WO | WO-/2008/124634 | 10/2008 |
| WO | WO-/2008/124639 | 10/2008 |
| WO | WO-2009070302 A1 | 6/2009 |
| WO | WO-2010/005721 | 1/2010 |
| WO | WO-2010/005723 | 1/2010 |
| WO | WO-2010/005726 | 1/2010 |
| WO | WO-2010005725 A2 | 1/2010 |
| WO | WO-2010/068866 | 6/2010 |
| WO | WO-2010075072 A2 | 7/2010 |
| WO | WO-2010/114770 | 10/2010 |
| WO | WO-2010114768 A1 | 10/2010 |
| WO | WO-2011/072218 | 6/2011 |

OTHER PUBLICATIONS

Brown, Dennis M. (editor); "Drug Delivery Systems in Cancer Therapy," 2004, Humana Press; Chapter 1, Ewesuedo, Reginald B.; and Ratain, Mark J. (authors); "Systemically Administered Drugs," pp. 3-14.*

Sweetman, Sean C.; "Martindale: The complete drug reference," 33$^{rd}$ ed., 2002; Pharmaceutical Press, entry for Docetaxel, p. 534.*

Maresca, K.P., et al., "A Series of Halogenated Heterodimeric Inhibitors of Prostate Specific Membrane Antigen (PSMA) as Radiolabeled Probes for Targeting Prostate Cancer," J. Med. Chem., 2009, vol. 52, No. 2, pp. 347-357.*

Gref, Ruxandra, et al., "Biodegradable Long-Circulating Polymeric Nanospheres," Science, 1994, vol. 263, pp. 1600-1603.

Caliceti, P., et al., "Effective Protein Release from PEG/PLA Nanoparticles Produced by Compressed Gas Anti-Solvent Precipitation Techniques," Journal of Controlled Release, 2004, vol. 94, pp. 195-205.

Yamamoto, Y., et al., "Long-Circulating Poly(ethylene glycol)-poly(D,L-lactide) block copolymer micelles with Modulated Surface Charge," Journal of Controlled Release, 2001, vol. 77, pp. 27-38.

Adams, M. et al., "Amphiphilic Block Copolymers for Drug Delivery," J. Pharm. Sci. (2003) 92(7):1343-1355.

Dancey, J.E. et al., "Therapeutic Targets: MTOR and Related Pathways," Cancer Biol. Ther. (2006) 5(9):1065-1073.

De Jaeghere, F. et al., "Freeze-Drying and Lyopreservation of Diblock and Triblock Poly(Lactic Acid)-Poly(Ethylene Oxide) (PLA-PEO) Copolymer Nanoparticles," Pharm. Dev. Technol. (2000) 5(4):473-483.

Gu, F. et al., "Precise Engineering of Targeted Nanoparticles by Using Self-Assembled Biointegrated Block Copolymers," Proc. Natl. Acad. Sci. USA. (2008) 105(7):2586-2591.

Heald, C.R. et al., "Poly(Lactic Acid)-Poly(Ethylene Oxide) (PLA-PEG) Nanoparticles: NMR Studies of the Central Solidlike PLA Core and the Liquid PEG Corona," Langmuir (2002) 18:3669-3675.

Jiang, X.Y. et al., "Preparation of PLA and PLGA Nanoparticles by Binary Organic Solvent Diffusion Method," J. Cent. South Univ. Technol. (2003) 10(3):202-206.

Pulkkinen, M. et al., "Three-Step Tumor Targeting of Paclitaxel Using Biotinylated PLA-PEG Nanoparticles and Avidin-Biotin Technology: Formulation Development and in Vitro Anticancer Activity," Eur. J. Pharm. Biopharm. (2008) 70:66-74.

Tobio, M. et al., "Stealth PLA-PEG Nanoparticles as Protein Carriers for Nasal Administration," Pharm. Res. (1998) 15(2):270-275.

Extended European Search Report for European Application No. 09794913.5 mailed Jul. 8, 2011.

International Search Report for Application No. PCT/US08/58873 dated Aug. 15, 2008 and mailed Aug. 28, 2008.

International Search Report for Application No. PCT/US09/47513 dated Jan. 18, 2010 and mailed Jan. 18, 2010.

International Search Report for Application No. PCT/US09/47515 dated Jan. 18, 2010 and mailed Jan. 19, 2010.

International Search Report for Application No. PCT/US09/47517 dated Feb. 25, 2010 and mailed Mar. 2, 2010.

International Search Report for Application No. PCT/US09/47518 dated Mar. 5, 2010 and mailed Mar. 5, 2010.

International Search Report for Application No. PCT/US09/67672 dated Aug. 20, 2010 and mailed Aug. 23, 2010.

International Search Report for Application No. PCT/US09/68028 dated Aug. 9, 2010 and mailed Aug. 23, 2010.

Barinka, Cyril, et al., "Interactions Between Human Glutamate Carboxypeptidase II and Urea-Based Inhibitors: Structural Characterization," J. Med. Chem. 2008, 51, 7737-7743, pp. 7737-7743.

Barinka, Cyril, et al., Strutural Insight into the Pharmacophore Pocket of Human Glutamate Carboxypeptidase II, J. Med. Chem. 2007, 50, pp. 3267-3273.

Chandran, Sachin S., et al., "Characterization of a Targeted Nanoparticle Functionalized with a Urea-Based Inhibitor of Prostate-Specific Membrane Antigen (PSMA)," Cancer Biology & Therapy 7:4, pp. 1-9; Apr. 2008.

Chen, Ying, et al., "Radiohalogenated Prostate-Specific Membrane Antigen (PSMA)-Based Ureas as Imaging Agents for Prostate Cancer," J. Med. Chem., 2008, 51 (24), pp. 7933-7943.

Farokhzad, Omid C., et al., "Nanoparticle-Aptamer Bioconjugates: A New Approach for Targeting Prostate Cancer Cells," Cancer Research 64, pp. 7668-7672, Nov. 1, 2004.

Foss, Catherine, Poster Session: Novel Probes and Activation Strategies, Part 3, "Synthesis and Validation of a Novel Small-Molecule Fluorescent Probe for PSMA Expression in Human Tumor Neovasculature," 4th Annual Meeting for the Society for Molecular Imaging, Sep. 7-10, 2005.

Foss, Catherine A., et al., "Radiolabeled Small-Molecule Ligands for Prostate-Specific Membrane Antigen: In Vivo Imaging in Experimental Models of Prostate Cancer," Clin. Cancer Res. 2005;11(11), pp. 4022-4028.

Humblet, Valerie, et al., "An HPLC/Mass Spectrometry Platform for the Development of Multimodality Contrast Agents and Targeted Therapeutics: Prostate-Specific Membrane Antigen Small Molecule Derivatives," Contrast Med. Mol. Imaging 1: pp. 196-211 (2006).

Humblet, Valerie, et al., "High-Affinity Near-Infrared Fluorescent Small-Molecule Contrast Agents for in Vivo Imaging of Prostate-Specific Membrane Antigen," Molecular Imaging, vol. 4, Oct. 2005, pp. 448-462.

Japaprakash, Sarva, et al., "Design and Synthesis of a PSMA Inhibitor-Doxorubicin Conjugate for Targeted Prostate Cancer Therapy," ChemMedChem 2006, 1, pp. 299-302.

Kozikowski, Alan P., et al., Design of Remarkably Simple, Yet Potent Urea-Based Inhibitors of Glutamate Carboxypeptidase II (NAALADase), J. Med. Chem, 2001, 44, pp. 298-301.

Kozikowski, Alan P., et al., "Synthesis of Urea-Based Inhibitors as Active Site Probes of Glutamate Carboxypeptidase II: Efficacy as Analgesic Agents," J. Med. Chem. 2004, 47, pp. 1729-1738.

Mease, Ronnie C., et al., "N-[N-[(S)-1,3-Dicarboxypropyl]Carbamoyl]-4[$^{18}$F] Fluorobenzyl-L-Cysteine, [$^{18}$F] DCFBC: A New Imaging Probe for Prostate Cancer," Clin. Cancer Res. 2008;14(10) May 15, 2008, pp. 3036-3043.

Misra, Preeti, et al., "Production of Multimeric Prostate-Specific Membrance Antigen Small-Molecule Radiotracers Using a Solid-Phase $^{99m}$ Tc Preloading Strategy," The Journal of Nuclear Medicine, vol. 48, No. 8, pp. 1379-1389., Aug. 2007.

Oliver, A. Jayne, et al., "Conformational and SAR Analysis of NAALADase and PSMA Inhibitors," Biorganic & Medicinal Chemistry 11 (2003) pp. 4455-4461.

Pomper, Martin G., Russell H. Morgan Department of Radiology and Radiological Science, Johns Hopkins University, "New Developments in Molecular Imaging of Prostate Cancer," Topical Symposium on: Advanced Molecular Imaging Techniques in the Detection, Diagnosis, Therapy, and Follow-up of Prostate Cancer, Palazzo Barberini, Rome, Dec. 6, 2005.

Tang, Hailun, et al., "Prostate Targeting Ligands Based on N-Acetylated α-Linked Acidic Dipeptidase," Biochemical and Biophysical Research Communications 307 (2003), pp. 8-14.

Zhou, Jia, et al., "NAAG Peptidase Inhibitors and Their Potential for Diagnosis and Therapy," Nature Reviews/Drug Discovery, vol. 4, Dec. 2005, pp. 1015-1025.

International Search Report for Application No. PCT/US08/13158 dated Jan. 20, 2009 and mailed Feb. 17, 2009.

* cited by examiner

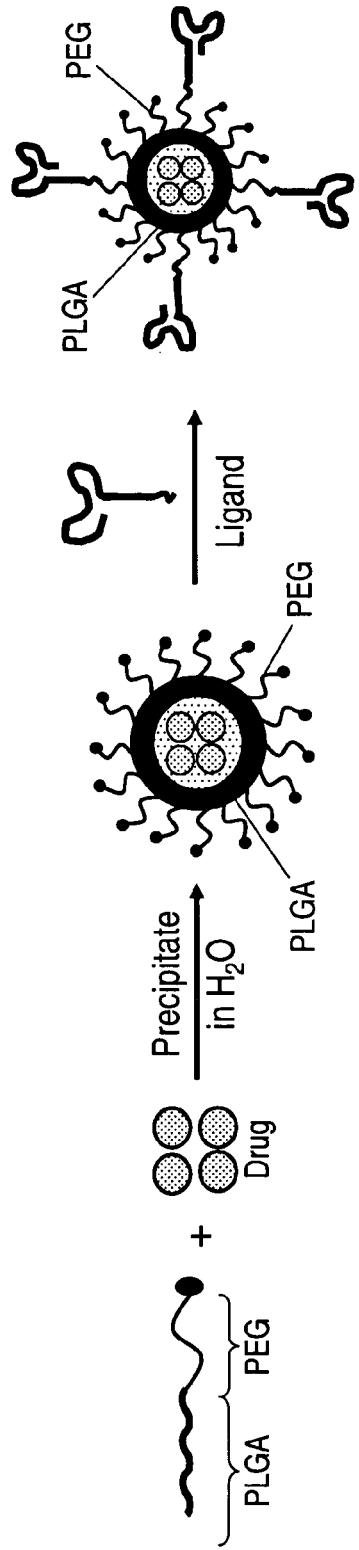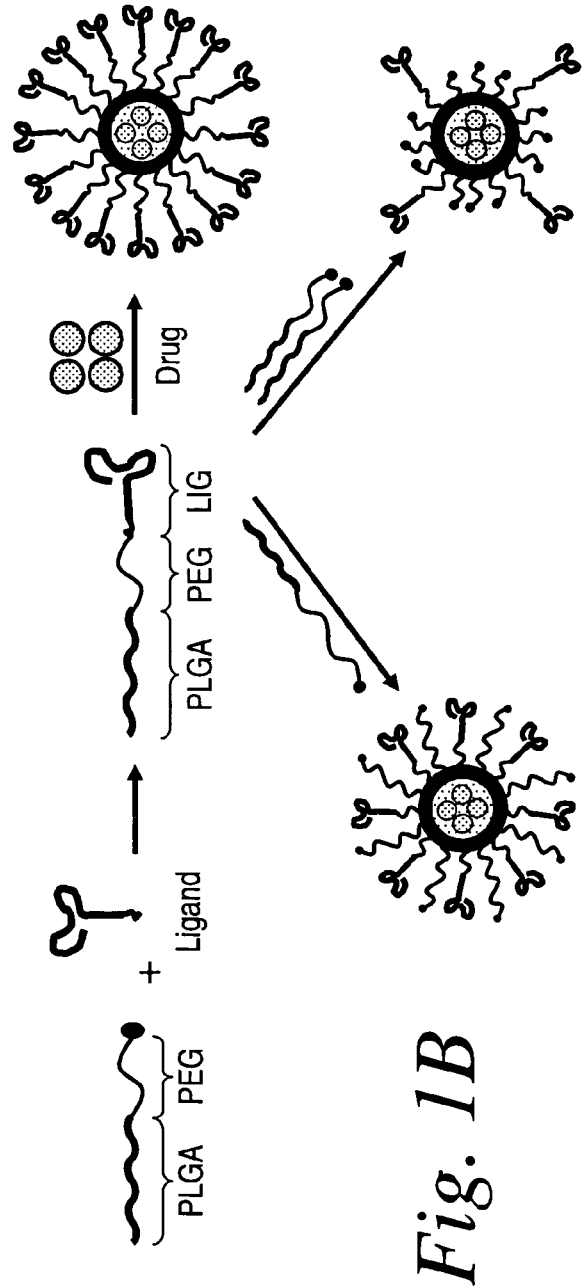
Fig. 1A
Fig. 1B

CANCER CELL TARGETING USING NANOPARTICLES

RELATED APPLICATIONS

This application claims priority to U.S. Provisional Application No. 60/976,197, filed Sep. 28, 2007, titled "CANCER CELL TARGETING USING NANOPARTICLES;" which is incorporated herein by reference in its entirety. Additionally, the contents of any patents, patent applications, and references cited throughout this specification are hereby incorporated by reference in their entireties.

FIELD OF INVENTION

The present invention generally relates to pharmaceutical compositions comprising target-specific stealth nanoparticles useful in the treatment of cancer.

BACKGROUND

The delivery of a drug to a patient with controlled-release of the active ingredient has been an active area of research for decades and has been fueled by the many recent developments in polymer science. In addition, controlled release polymer systems can be designed to provide a drug level in the optimum range over a longer period of time than other drug delivery methods, thus increasing the efficacy of the drug and minimizing problems with patient compliance.

Biodegradable particles have been developed as sustained release vehicles used in the administration of small molecule drugs, proteins and peptide drugs, and nucleic acids. The drugs are typically encapsulated in a polymer matrix which is biodegradable and biocompatible. As the polymer is degraded and/or as the drug diffuses out of the polymer, the drug is released into the body.

Targeting controlled release polymer systems (e.g., targeted to a particular tissue or cell type or targeted to a specific diseased tissue but not normal tissue) is desirable because it reduces the amount of a drug present in tissues of the body that are not targeted. This is particularly important when treating a condition such as cancer where it is desirable that a cytotoxic dose of the drug is delivered to cancer cells without killing the surrounding non-cancerous tissue. Effective drug targeting should reduce the undesirable and sometimes life threatening side effects common in anticancer therapy. In addition, targeting may allow drugs to reach certain tissues they would otherwise be unable to reach without a targeted nanoparticle.

Accordingly, a need exists to develop delivery systems which can deliver therapeutic levels of drug to treat diseases such as cancer, while also reducing patient side effects.

SUMMARY OF THE INVENTION

There remains a need for compositions useful in the treatment or prevention or amelioration of one or more symptoms of cancer, particularly cancers that express prostate specific membrane antigen (PSMA), including, but not limited to, prostate cancer, non-small cell lung cancer, colorectal carcinoma, and glioblastoma, and solid tumors expressing PSMA in the tumor neovasculature. In one aspect, the invention provides a pharmaceutical composition comprising a plurality of target-specific stealth nanoparticles that comprise a therapeutic agent; wherein said nanoparticles contain targeting moieties attached thereto, wherein the targeting moiety is a low-molecular weight PSMA ligand.

In one embodiment of the pharmaceutical composition of the invention, the nanoparticle has an amount of targeting moiety effective for the treatment of prostate cancer in a subject in need thereof. In another embodiment, the nanoparticle has an amount of targeting moiety effective for the treatment of solid tumors expressing PSMA in the tumor neovasculature in a subject in need thereof. In yet another embodiment, the low-molecular weight PSMA ligand has a $K_i$ of between 0.5 nM and 10 nM.

In one embodiment of the pharmaceutical composition of the invention, the nanoparticle has an amount of therapeutic agent effective for the treatment of prostate cancer in a subject in need thereof. In another embodiment, the nanoparticle has an amount of therapeutic agent effective for the treatment of solid tumors expressing PSMA in the tumor neovasculature in a subject in need thereof.

In another embodiment of the target-specific stealth nanoparticles of the invention, the low-molecular weight PSMA ligand has a molecular weight of less than 1000 g/mol. In particular embodiments, the low-molecular weight PSMA ligand is selected from the group consisting of compounds I, II, III and IV. In other embodiments, the low-molecular weight PSMA ligand is

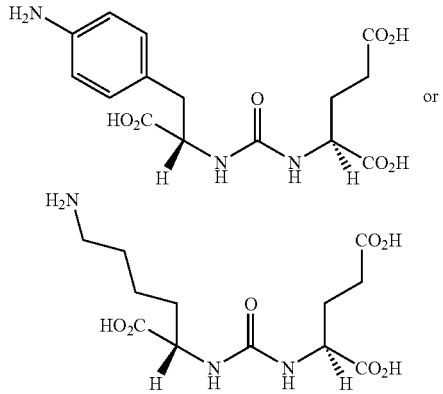

and enantiomers, stereoisomers, rotamers, tautomers, diastereomers, or racemates thereof.

In other embodiments of the target-specific stealth nanoparticles of the invention, the nanoparticle comprises a polymeric matrix. In one embodiment, the polymeric matrix comprises two or more polymers. In another embodiment, the polymeric matrix comprises polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, or combinations thereof. In still another embodiment, the polymeric matrix comprises one or more polyesters, polyanhydrides, polyethers, polyurethanes, polymethacrylates, polyacrylates or polycyanoacrylates. In another embodiment, at least one polymer is a polyalkylene glycol. In still another embodiment, the polyalkylene glycol is polyethylene glycol. In yet another embodiment, at least one polymer is a polyester. In another embodiment, the polyester is selected from the group consisting of PLGA, PLA, PGA, and polycaprolactones. In still another embodiment, the polyester is PLGA or PLA. In yet another embodiment, the polymeric matrix comprises a copolymer of two or more polymers. In another embodiment, the copolymer is a copolymer of a polyalkylene glycol and a polyester. In still another embodiment, the copolymer is a copolymer of PLGA or PLA and PEG. In yet another embodiment, the polymeric matrix comprises PLGA or PLA and a copolymer of PLGA or PLA and PEG.

In another embodiment, the polymeric matrix comprises a lipid-terminated polyalkylene glycol and a polyester. In another embodiment of the pharmaceutical composition of the invention, the polymeric matrix comprises lipid-terminated PEG and PLGA. In one embodiment, the lipid is of the Formula V. In a particular embodiment, the lipid is 1,2 distearoyl-sn-glycero-3-phosphoethanolamine (DSPE), and salts thereof, e.g., the sodium salt.

In another embodiment of the pharmaceutical composition of the invention, a portion of the polymer matrix is covalently bound to the low-molecular weight PSMA ligand. In another embodiment, the polymer matrix is covalently bound to the low-molecular weight PSMA ligand via the free terminus of PEG. In still another embodiment, the polymer matrix is covalently bound to the low-molecular weight PSMA ligand via a carboxyl group at the free terminus of PEG. In yet another embodiment, the polymer matrix is covalently bound to the low-molecular weight PSMA ligand via a maleimide functional group at the free terminus of PEG.

In another embodiment of the pharmaceutical composition of the invention, the nanoparticle has a ratio of ligand-bound polymer to non-functionalized polymer effective for the treatment of prostate cancer. In another embodiment, the polymers of the polymer matrix have a molecular weight effective for the treatment of prostate cancer. In still another embodiment, the nanoparticle has a surface charge effective for the treatment of prostate cancer.

In another embodiment of the pharmaceutical composition of the invention, said system is suitable for target-specific treatment of a disease or disorder and delivery of a therapeutic agent. In another embodiment, the nanoparticle further comprises a therapeutic agent. In one embodiment, the therapeutic agent is associated with the surface of, encapsulated within, surrounded by, or dispersed throughout the nanoparticle. In still another embodiment, the therapeutic agent is encapsulated within the hydrophobic core of the nanoparticle. In particular embodiments, the therapeutic agent is selected from the group consisting of mitoxantrone and docetaxel.

In another aspect, the invention provides a method of treating prostate cancer in a subject in need thereof, comprising administering to the subject an effective amount of the pharmaceutical composition of the invention. In one embodiment, the pharmaceutical composition is administered directly to the prostate of a subject. In still another embodiment, the pharmaceutical composition is administered directly to prostate cancer cells. In another embodiment, the pharmaceutical composition is administered directly to prostate cancer cells by injection into tissue comprising the prostate cancer cells. In yet another embodiment, the pharmaceutical composition is administered to the subject by implantation of nanoparticles at or near prostate cancer cells during surgical removal of a tumor. In another embodiment, the pharmaceutical composition is administered systemically, or via intravenous administration.

In another aspect, the invention provides a method of preparing a stealth nanoparticle, wherein the nanoparticle has a ratio of ligand-bound polymer to non-functionalized polymer effective for the treatment of prostate cancer, comprising: providing a therapeutic agent; providing a polymer; providing a low-molecular weight PSMA ligand; mixing the polymer with the therapeutic agent to prepare particles; and associating the particles with the low-molecular weight PSMA ligand. In one embodiment of the method, the polymer comprises a copolymer of two or more polymers. In another embodiment, the copolymer is a copolymer of PLGA and PEG or PLA and PEG.

In another aspect, the invention provides a method of preparing a stealth nanoparticle, wherein the nanoparticle has a ratio of ligand-bound polymer to non-functionalized polymer effective for the treatment of prostate cancer, comprising: providing a therapeutic agent; providing a first polymer; providing a low-molecular weight PSMA ligand; reacting the first polymer with the low-molecular weight PSMA ligand to prepare a ligand-bound polymer; and mixing the ligand-bound polymer with a second, non-functionalized polymer, and the therapeutic agent; such that the stealth nanoparticle is formed. In one embodiment of this method, the first polymer comprises a copolymer of two or more polymers. In another embodiment, the second, non-functionalized polymer comprises a copolymer of two or more polymers.

In an embodiment of the methods described above, the copolymer is a copolymer of PLGA and PEG, or PLA and PEG. In another embodiment, the first polymer is a copolymer of PLGA and PEG, wherein the PEG has a carboxyl group at the free terminus. In another embodiment, the first polymer is first reacted with a lipid, to form a polymer/lipid conjugate, which is then mixed with the low-molecular weight PSMA ligand. In still another embodiment, the lipid is 1,2 distearoyl-sn-glycero-3-phosphoethanolamine (DSPE), and salts thereof, e.g., the sodium salt.

In another embodiment of the pharmaceutical composition of the invention, the nanoparticle has an amount of targeting moiety effective for the treatment of a cancer wherein PSMA is expressed on the surface of cancer cells or in the tumor neovasculature in a subject in need thereof. In one embodiment, the PSMA-related indication is selected from the group consisting of prostate cancer, non-small cell lung cancer, colorectal carcinoma, and glioblastoma.

In another aspect, the invention provides a stealth nanoparticle, comprising a copolymer of PLGA and PEG; and a therapeutic agent comprising mitoxantrone or docetaxel; wherein said nanoparticle contains targeting moieties attached thereto, wherein the targeting moiety is a low-molecular weight PSMA ligand.

In another aspect, the invention provides a stealth nanoparticle, comprising a polymeric matrix comprising a complex of a phospholipid bound-PEG and PLGA; and a therapeutic agent; wherein said nanoparticle contains targeting moieties attached thereto, wherein the targeting moiety is a low-molecular weight PSMA ligand. In one embodiment of this stealth nanoparticle, the therapeutic agent is mitoxantrone or docetaxel.

In particular embodiments of the stealth nanoparticles described above, the low-molecular weight PSMA ligand is

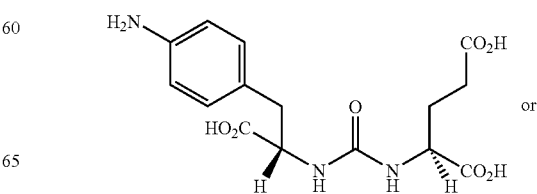

-continued

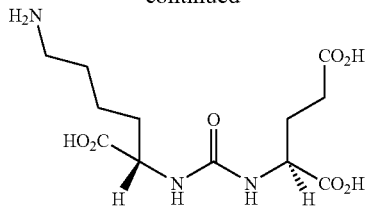

and enantiomers, stereoisomers, rotamers, tautomers, diastereomers, or racemates thereof.

In another aspect, the invention provides a targeted particle, comprising: a targeting moiety, and a therapeutic agent; wherein the particle comprises a polymeric matrix, wherein the polymeric matrix comprises a polyester, and wherein the targeting moiety is a low-molecular weight PSMA ligand. In one embodiment of this targeted particle, the particle is a nanoparticle. In another embodiment, the polyester is selected from the group consisting of PLGA, PLA, PGA, polycaprolactone, and polyanhydrides. In one embodiment of the polymeric matrix of this targeted particle, at least one polymer is polyalkylene glycol. In certain embodiments of the targeted particle, the a low-molecular weight PSMA ligand is selected from the group consisting of folic acid, thiol and indole thiol derivatives, hydroxamate derivatives, and urea-based inhibitors.

In another aspect, the invention provides a composition, comprising: a particle having an average characteristic dimension of less than about 1 micrometer, the particle comprising a macromolecule comprising a first portion comprising a biocompatible polymer and a second portion comprising a moiety selected from the group consisting of a targeting moiety, and a therapeutic moiety, wherein the targeting moiety is a low-molecular weight PSMA ligand, and wherein the targeting moiety has an essentially nonzero concentration internally of the particle, i.e., there is little to no detectable amount of the compound present in the interior of the particle. In one embodiment of this particle, the biocompatible polymer comprises poly(lactide-co-glycolide). In another embodiment of this particle, the polymer comprises poly(ethylene glycol).

In one embodiment, the invention comprises a nanoparticle comprising a low molecular weight PSMA ligand, a biodegradable polymer, a stealth polymer, and a therapeutic agent. In one embodiment, the invention comprises a nanoparticle comprising a low molecular weight PSMA ligand, a biodegradable polymer, a stealth polymer, and a therapeutic agent, wherein the nanoparticle can selectively accumulate in the prostate or in the vascular endothelial tissue surrounding a cancer. In one embodiment, the invention comprises a nanoparticle comprising a low molecular weight PSMA ligand, a biodegradable polymer, a stealth polymer, and a therapeutic agent, wherein the nanoparticle can selectively accumulate in the prostate or in the vascular endothelial tissue surrounding a cancer and wherein the nanoparticle can be endocytosed by a PSMA expressing cell. In another embodiment, the invention comprises a nanoparticle comprising a low molecular weight PSMA ligand, a biodegradable polymer, polyethylene glycol, and a chemotherapeutic agent. In another embodiment, the invention comprises a nanoparticle comprising a low molecular weight PSMA ligand, a biodegradable polymer, polyethylene glycol, and docetaxel. In another embodiment, the invention comprises a nanoparticle comprising a low molecular weight PSMA ligand, PLGA, polyethylene glycol, and docetaxel.

In one aspect, the invention provides a target-specific stealth nanoparticle comprising a therapeutic agent; wherein the nanoparticle contains targeting moieties attached thereto, wherein the targeting moiety is a low-molecular weight PSMA ligand, and wherein the therapeutic agent is an siRNA. In another aspect, the siRNA molecule is complementary to tumor-related targets, e.g., a prostate tumor.

BRIEF DESCRIPTION OF THE DRAWINGS

FIGS. 1A, 1B, and 2 show representative synthesis schematics for the target-specific stealth nanoparticles of the invention.

DETAILED DESCRIPTION OF THE INVENTION

Figure 2:
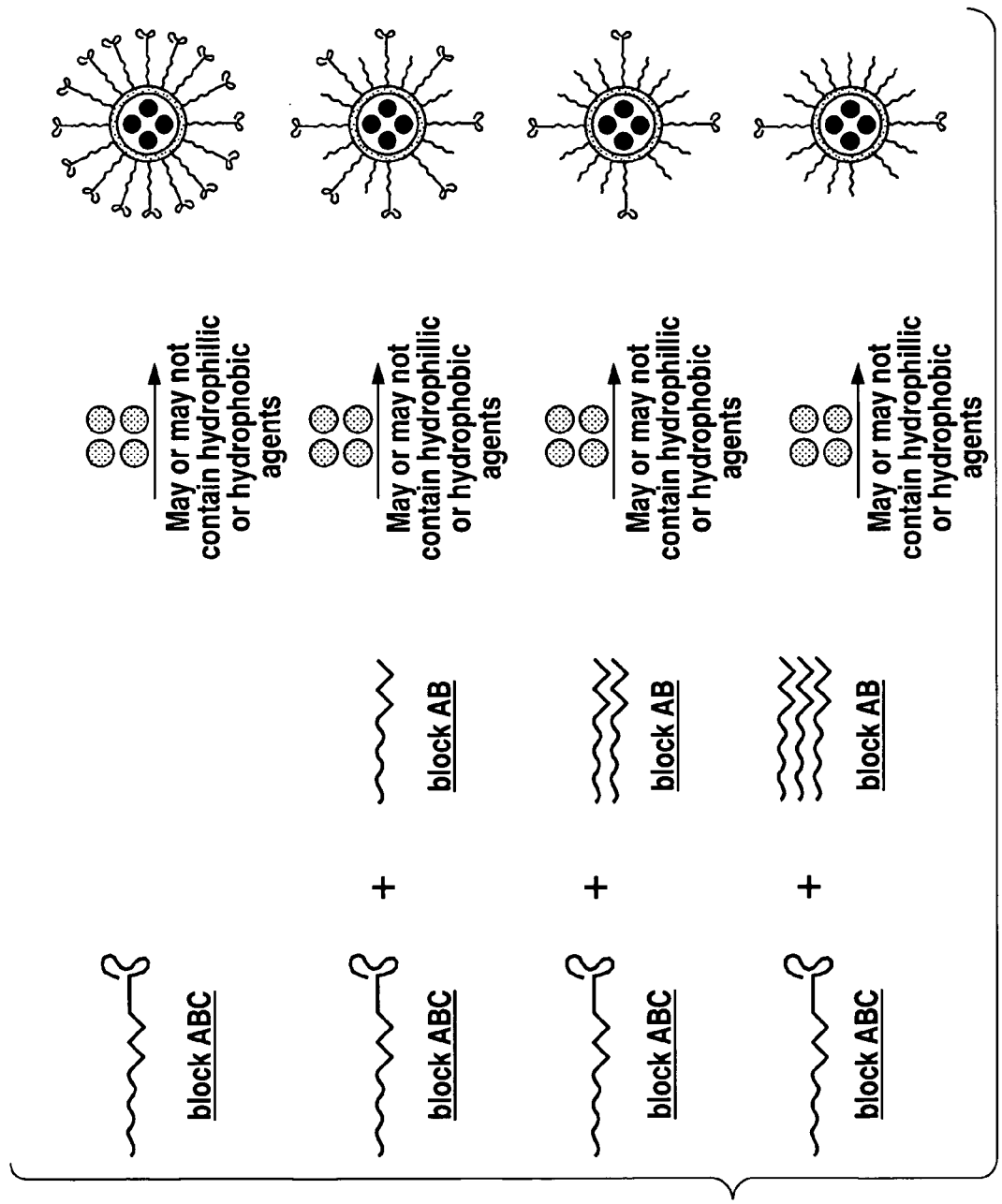

The present invention generally relates to particles, and, in particular, nanoparticles, wherein the nanoparticles comprise a controlled-release system for the targeted delivery of a therapeutic agent. One aspect of the invention is directed to a method of developing polymeric nanoparticles with desired properties, wherein the nanoparticles contain a targeting moiety that is a low-molecular weight PSMA ligand. In one set of embodiments, the method includes producing libraries of nanoparticles containing low-molecular weight PSMA ligands, wherein the libraries have highly controlled properties, and wherein the libraries can be formed by mixing together two or more polymers (e.g., ligand-functionalized polymers and non-functionalized polymers) in different ratios. One or more of the polymers may be a biocompatible polymer (e.g., homopolymer, copolymer or block copolymer), wherein the biocompatible polymer may be conjugated to a low-molecular weight PSMA ligand. In some cases, the nanoparticle may contain a therapeutic agent, e.g., a drug.

In one embodiment, the nanoparticle of the controlled release system has an amount of targeting moiety (i.e., a low-molecular weight PSMA ligand) effective for the treatment of prostate cancer in a subject in need thereof. In certain embodiments, the low-molecular weight PSMA ligand is conjugated to a polymer, and the nanoparticle comprises a certain ratio of ligand-conjugated polymer to non-functionalized polymer. The nanoparticle can have an optimized ratio of these two polymers, such that an effective amount of ligand is associated with the nanoparticle for treatment of cancer. For example, increased ligand density (e.g., on a PLGA-PEG copolymer) will increase target binding (cell binding/target uptake), making the nanoparticle "target specific." Alternatively, a certain concentration of non-functionalized polymer (e.g., non-functionalized PLGA-PEG copolymer) in the nanoparticle can control inflammation and/or immunogenicity (i.e., the ability to provoke an immune response), and allow the nanoparticle to have a circulation half-life that is adequate for the treatment of cancer (e.g., prostate cancer). Furthermore, the non-functionalized polymer can lower the rate of clearance from the circulatory system via the reticuloendothelial system (RES). Thus, the non-functionalized polymer gives the nanoparticle "stealth" characteristics. In a particular embodiment, the stealth polymer is PEG. Additionally, the non-functionalized polymer balances an otherwise high concentration of ligands, which can otherwise accelerate clearance by the subject, resulting in less delivery to the target cells.

By having targeting moieties, the "target specific" nanoparticles are able to efficiently bind to or otherwise associate with a biological entity, for example, a membrane component or cell surface receptor. Targeting of a therapeutic agent (e.g., to a particular tissue or cell type, to a specific diseased tissue but not to normal tissue, etc.) is desirable for the treatment of tissue specific diseases such as cancer (e.g. prostate cancer). For example, in contrast to systemic delivery of a cytotoxic anti-cancer agent, targeted delivery could prevent the agent from killing healthy cells. Additionally, targeted delivery would allow for the administration of a lower dose of the agent, which could reduce the undesirable side effects commonly associated with traditional chemotherapy. As discussed above, the target specificity of the nanoparticles of the invention will be maximized by optimizing the ligand density on the nanoparticle.

Target-Specific Stealth Nanoparticles Comprising Polymers

In some embodiments, the nanoparticles of the invention comprise a matrix of polymers. In general, a "nanoparticle" refers to any particle having a diameter of less than 1000 nm. In some embodiments, a therapeutic agent and/or targeting moiety (i.e., a low-molecular weight PSMA ligand) can be associated with the polymeric matrix. In some embodiments, the targeting moiety can be covalently associated with the surface of a polymeric matrix. In some embodiments, covalent association is mediated by a linker. In some embodiments, the therapeutic agent can be associated with the surface of, encapsulated within, surrounded by, and/or dispersed throughout the polymeric matrix.

A wide variety of polymers and methods for forming particles therefrom are known in the art of drug delivery. In some embodiments of the invention, the matrix of a particle comprises one or more polymers. Any polymer may be used in accordance with the present invention. Polymers may be natural or unnatural (synthetic) polymers. Polymers may be homopolymers or copolymers comprising two or more monomers. In terms of sequence, copolymers may be random, block, or comprise a combination of random and block sequences. Typically, polymers in accordance with the present invention are organic polymers.

A "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer is biologically derived, i.e., a biopolymer. Non-limiting examples of polymers include peptides or proteins (i.e., polymers of various amino acids), or nucleic acids such as DNA or RNA, as discussed below. In some cases, additional moieties may also be present in the polymer, for example biological moieties such as those described below.

If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a "block" copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

It should be understood that, although the terms "first," "second," etc. may be used herein to describe various elements, including polymeric components, these terms should not be construed as being limiting (e.g., describing a particular order or number of elements), but rather, as being merely descriptive, i.e., labels that distinguish one element from another, as is commonly used within the field of patent law. Thus, for example, although one embodiment of the invention may be described as having a "first" element present and a "second" element present, other embodiments of the invention may have a "first" element present but no "second" element present, a "second" element present but no "first" element present, two (or more) "first" elements present, and/or two (or more) "second" elements present, etc., and/or additional elements such as a "first" element, a "second" element, and a "third" element, without departing from the scope of the present invention.

Various embodiments of the present invention are directed to copolymers, which, in particular embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer is a first block of the block copolymer and the second polymer is a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers.

For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, the polymer (e.g., copolymer, e.g., block copolymer) is amphiphilic, i.e., having a hydrophilic portion and a hydrophobic portion, or a relatively hydrophilic portion and a relatively hydrophobic portion. A hydrophilic polymer is one generally that attracts water and a hydrophobic polymer is one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about 60°). In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymer (e.g., copolymer, e.g., block copolymer) of the present invention includes a biocompatible polymer, i.e., the polymer that does not typically induce an adverse response when inserted or injected into a living subject, for example, without significant inflammation and/or acute rejection of the polymer by the immune system, for instance, via a T-cell response. It will be recognized, of course, that "biocompatibility" is a relative term, and some degree of immune response is to be expected even for polymers that are highly compatible with living tissue. However, as used herein, "biocompatibility" refers to the acute rejection of material by at least a portion of the immune system, i.e., a non-biocompatible material implanted into a subject provokes an immune response in the subject that is severe enough such that the rejection of the material by the immune system cannot be adequately controlled, and often is of a degree such that the material must be removed from the subject. One simple test to determine biocompatibility is to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments of the present invention include polydioxanone (PDO), polyhydroxyalkanoate, polyhydroxybutyrate, poly(glycerol sebacate), polyglycolide, polylactide, PLGA, polycaprolactone, or copolymers or derivatives including these and/or other polymers.

In certain embodiments, the biocompatible polymer is biodegradable, i.e., the polymer is able to degrade, chemically and/or biologically, within a physiological environment, such as within the body. For instance, the polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic acid-co-glycolic acid) and poly (lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene inline), PEGylated poly(ethylene imine), poly(L-lactide-co-L-lysine), poly(serine ester), poly (4-hydroxy-L-proline ester), poly[a-(4-aminobutyl)-L-glycolic acid], and derivatives thereof.

In some embodiments, the polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In particular embodiments, by optimizing the ratio of lactic acid to glycolic acid monomers in the polymer of the nanoparticle (e.g., the PLGA block copolymer or PLGA-PEG block copolymer), nanoparticle parameters such as water uptake, therapeutic agent release (e.g., "controlled release") and polymer degradation kinetics can be optimized.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, RNA, or derivatives thereof). Amine-containing polymers such as poly(lysine) (Zauner et al., 1998, *Adv. Drug Del. Rev.*, 30:97; and Kabanov et al., 1995, *Bioconjugate Chem.*, 6:7), poly(ethylene imine) (PEI; Boussif et al, 1995, *Proc. Natl. Acad. Sci., USA,* 1995, 92:7297), and poly(amidoamine) dendrimers (Kukowska-Latallo et al., 1996, *Proc. Natl. Acad. Sci., USA,* 93:4897; Tang et al., 1996, *Bioconjugate Chem.,* 7:703; and Haensler et al., 1993, *Bioconjugate Chem.,* 4:372) are positively-charged at physiological pH, form ion pairs with nucleic acids, and mediate transfection in a variety of cell lines.

In some embodiments, polymers can be degradable polyesters bearing cationic side chains (Putnam et al., 1999, *Macromolecules,* 32:3658; Barrera et al., 1993, *J. Am. Chem. Soc.,* 115:11010; Urn et al., 1999, *J. Am. Chem. Soc.,* 121:5633; and Zhou et al, 1990, *Macromolecules,* 23:3399). Examples of these polyesters include poly(L-lactide-co-L-lysine) (Barrera et al, 1993, *J. Am. Chem. Soc.,* 115:11010), poly(serine ester) (Zhou et al, 1990, *Macromolecules,* 23:3399), poly(4-hydroxy-L-proline ester) (Putnam et al, 1999, *Macromolecules,* 32:3658; and Lim et al, 1999, *J. Am. Chem. Soc.,* 121:5633). Poly(4-hydroxy-L-proline ester) was demonstrated to condense plasmid DNA through electrostatic interactions, and to mediate gene transfer (Putnam et al, 1999, *Macromolecules,* 32:3658; and Lim et al, 1999, *J. Am. Chem. Soc.,* 121:5633). These new polymers are less toxic than poly(lysine) and PEI, and they degrade into non-toxic metabolites.

A polymer (e.g., copolymer, e.g., block copolymer) containing poly(ethylene glycol) repeat units is also referred to as a "PEGylated" polymer. Such polymers can control inflammation and/or immunogenicity (i.e., the ability to provoke an immune response) and/or lower the rate of clearance from the circulatory system via the reticuloendothelial system (RES), due to the presence of the poly(ethylene glycol) groups.

PEGylation may also be used, in some cases, to decrease charge interaction between a polymer and a biological moiety, e.g., by creating a hydrophilic layer on the surface of the polymer, which may shield the polymer from interacting with the biological moiety. In some cases, the addition of poly (ethylene glycol) repeat units may increase plasma half-life of the polymer (e.g., copolymer, e.g., block copolymer), for instance, by decreasing the uptake of the polymer by the phagocytic system while decreasing transfection/uptake efficiency by cells. Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, by ring opening polymerization techniques (ROMP), or the like.

In addition, certain embodiments of the invention are directed towards copolymers containing poly(ester-ether)s, e.g., polymers having repeat units joined by ester bonds (e.g., R—C(O)—O—R' bonds) and ether bonds (e.g., R—O—R' bonds). In some embodiments of the invention, a biodegradable polymer, such as a hydrolyzable polymer, containing carboxylic acid groups, may be conjugated with poly(ethylene glycol) repeat units to form a poly(ester-ether).

In a particular embodiment, the molecular weight of the polymers of the nanoparticles of the invention are optimized for effective treatment of cancer, e.g., prostate cancer. For example, the molecular weight of the polymer influences nanoparticle degradation rate (particularly when the molecular weight of a biodegradable polymer is adjusted), solubility, water uptake, and drug release kinetics (e.g. "controlled release"). As a further example, the molecular weight of the polymer can be adjusted such that the nanoparticle biodegrades in the subject being treated within a reasonable period of time (ranging from a few hours to 1-2 weeks, 3-4 weeks, 5-6 weeks, 7-8 weeks, etc.). In particular embodiments of a nanoparticle comprising a copolymer of PEG and PLGA, the PEG has a molecular weight of 1,000-20,000, e.g., 5,000-20,000, e.g., 10,000-20,000, and the PLGA has a molecular weight of 5,000-100,000, e.g., 20,000-70,000, e.g., 20,000-50,000.

In certain embodiments, the polymers of the nanoparticles may be conjugated to a lipid. The polymer may be, for example, a lipid-terminated PEG. As described below, the lipid portion of the polymer can be used for self assembly with another polymer, facilitating the formation of a nanoparticle. For example, a hydrophilic polymer could be conjugated to a lipid that will self assemble with a hydrophobic polymer.

In some embodiments, lipids are oils. In general, any oil known in the art can be conjugated to the polymers used in the invention. In some embodiments, an oil may comprise one or more fatty acid groups or salts thereof. In some embodiments, a fatty acid group may comprise digestible, long chain (e.g., $C_8$-$C_{50}$), substituted or unsubstituted hydrocarbons. In some embodiments, a fatty acid group may be a $C_{10}$-$C_{20}$ fatty acid or salt thereof. In some embodiments, a fatty acid group may be a $C_{15}$-$C_{20}$ fatty acid or salt thereof. In some embodiments, a fatty acid may be unsaturated. In some embodiments, a fatty acid group may be monounsaturated. In some embodiments, a fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

In a particular embodiment, the lipid is of the Formula V:

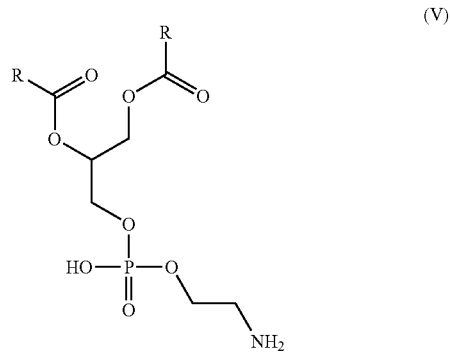

(V)

and salts thereof, wherein each R is, independently, $C_{1-30}$ alkyl. In one embodiment of Formula V, the lipid is 1,2 distearoyl-sn-glycero-3-phosphoethanolamine (DSPE), and salts thereof, e.g., the sodium salt.

In one embodiment, the small molecule targeting moieties are bonded, e.g., covalently bonded, to the lipid component of the nanoparticle. Thus, the invention also provides a target-specific stealth nanoparticle comprising a therapeutic agent, a polymeric matrix, a lipid, and a low-molecular weight PSMA targeting ligand, wherein the targeting ligand is bonded, e.g., covalently bonded, to the lipid component of the nanoparticle. In one embodiment, the lipid component that is bonded to the low-molecular weight targeting moiety is of the Formula V. In another embodiment, the invention provides a target-specific stealth nanoparticle comprising a therapeutic agent, a polymermeric matrix, DSPE, and a low-molecular weight PSMA targeting ligand, wherein the ligand is bonded, e.g., covalently bonded, to DSPE. For example, the nanoparticle of the invention comprises a polymeric matrix comprising PLGA-DSPE-PEG-Ligand. These nanoparticles can be used for the treatment of the diseases and disorders discussed herein.

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al, 2001, *J. Am. Chem. Soc.*, 123:9480; Lim et al., 2001, *J. Am. Chem. Soc.*, 123:2460; Langer, 2000, *Ace. Chem. Res.*, 33:94; Langer, 1999, *J. Control. Release*, 62:7; and Uhrich et al., 1999, *Chem. Rev.*, 99:3181). More generally, a variety of methods for synthesizing suitable polymers are described in *Concise Encyclopedia of Polymer Science and Polymeric Amines and Ammonium Salts*, Ed. by Goethals, Pergamon Press, 1980; *Principles of Polymerization by Odian*, John Wiley & Sons, Fourth Edition, 2004; *Contemporary Polymer Chemistry* by Allcock et al., Prentice-Hall, 1981; Deming et al, 1997, *Nature*, 390:386; and in U.S. Pat. Nos. 6,506,577, 6,632,922, 6,686,446, and 6,818,732.

In still another set of embodiments, a particle (comprising, e.g., a copolymer, e.g., a block copolymer) of the present invention includes a therapeutic moiety, i.e., a moiety that has a therapeutic or prophylactic effect when given to a subject.

Examples of therapeutic moieties to be used with the nanoparticles of the present invention include antineoplastic or cytostatic agents or other agents with anticancer properties, or a combination thereof.

In some cases, the particle is a nanoparticle, i.e., the particle has a characteristic dimension of less than about 1 micrometer, where the characteristic dimension of a particle is the diameter of a perfect sphere having the same volume as the particle. For example, the particle may have a characteristic dimension of the particle may be less than about 300 nm, less than about 200 nm, less than about 150 nm, less than about 100 nm, less than about 50 nm, less than about 30 nm, less than about 10 nm, less than about 3 nm, or less than about 1 nm in some cases. In particular embodiments, the nanoparticle of the present invention has a diameter of 80 nm-200 nm.

In one set of embodiments, the particles may have an interior and a surface, where the surface has a composition different from the interior, i.e., there may be at least one compound present in the interior but not present on the surface (or vice versa), and/or at least one compound is present in the interior and on the surface at differing concentrations. For example, in one embodiment, a compound, such as a targeting moiety (i.e., a low-molecular weight PSMA ligand) of a polymeric conjugate of the present invention, may be present in both the interior and the surface of the particle, but at a higher concentration on the surface than in the interior of the particle, although in some cases, the concentration in the interior of the particle may be essentially nonzero, i.e., there is a detectable amount of the compound present in the interior of the particle.

In some cases, the interior of the particle is more hydrophobic than the surface of the particle. For instance, the interior of the particle may be relatively hydrophobic with respect to the surface of the particle, and a drug or other payload may be hydrophobic, and readily associates with the relatively hydrophobic center of the particle. The drug or other payload may thus be contained within the interior of the particle, which may thus shelter it from the external environment surrounding the particle (or vice versa). For instance, a drug or other payload contained within a particle administered to a subject will be protected from a subject's body, and the body will also be isolated from the drug. A targeting moiety present on the surface of the particle may allow the particle to become localized at a particular targeting site, for instance, a tumor, a disease site, a tissue, an organ, a type of cell, etc. As such, the nanoparticle is "target specific." The drug or other payload may then, in some cases, be released from the particle and allowed to interact locally with the particular targeting site.

Yet another aspect of the invention is directed to polymer particles having more than one polymer or macromolecule present, and libraries involving such polymers or macromolecules. For example, in one set of embodiments, particles may contain more than one distinguishable polymers (e.g., copolymers, e.g., block copolymers), and the ratios of the two (or more) polymers may be independently controlled, which allows for the control of properties of the particle. For instance, a first polymer may be a polymeric conjugate comprising a targeting moiety and a biocompatible portion, and a second polymer may comprise a biocompatible portion but not contain the targeting moiety, or the second polymer may contain a distinguishable biocompatible portion from the first polymer. Control of the amounts of these polymers within the polymeric particle may thus be used to control various physical, biological, or chemical properties of the particle, for instance, the size of the particle (e.g., by varying the molecular weights of one or both polymers), the surface charge (e.g., by controlling the ratios of the polymers if the polymers have different charges or terminal groups), the surface hydrophilicity (e.g., if the polymers have different molecular weights and/or hydrophilicities), the surface density of the targeting moiety (e.g., by controlling the ratios of the two or more polymers), etc.

As a specific example, a particle may comprise a first polymer comprising a poly(ethylene glycol) and a targeting moiety conjugated to the poly(ethylene glycol), and a second polymer comprising the poly(ethylene glycol) but not the targeting moiety, or comprising both the poly(ethylene glycol) and the targeting moiety, where the poly(ethylene glycol) of the second polymer has a different length (or number of repeat units) than the poly(ethylene glycol) of the first polymer. As another example, a particle may comprise a first polymer comprising a first biocompatible portion and a targeting moiety, and a second polymer comprising a second biocompatible portion different from the first biocompatible portion (e.g., having a different composition, a substantially different number of repeat units, etc.) and the targeting moiety. As yet another example, a first polymer may comprise a biocompatible portion and a first targeting moiety, and a second polymer may comprise a biocompatible portion and a second targeting moiety different from the first targeting moiety.

In other embodiments, the nanoparticles of the invention are liposomes, liposome polymer combinations, dendrimers, and albumin particles that are functionalized with a low-molecular weight PSMA ligand. These nanoparticles can be used to deliver a therapeutic agent to a subject, such as an anti-cancer agent like mitoxantrone or docetaxel.

As used herein, the term "liposome" refers to a generally spherical vesicle or capsid generally comprised of amphipathic molecules (e.g., having both a hydrophobic (nonpolar) portion and a hydrophilic (polar) portion). Typically, the liposome can be produced as a single (unilamellar) closed bilayer or a multicompartment (multilamellar) closed bilayer. The liposome can be formed by natural lipids, synthetic lipids, or a combination thereof. In a preferred embodiment, the liposome comprises one or more phospholipids. Lipids known in the art for forming liposomes include, but are not limited to, lecithin (soy or egg; phosphatidylcholine), dipalmitoylphosphatidylcholine, dimyristoylphosphatidylcholine, distearoylphosphatidylcholine, dicetylphosphate, phosphatidylglycerol, hydrogenated phosphatidylcholine, phosphatidic acid, cholesterol, phosphatidylinositol, a glycolipid, phosphatidylethanolamine, phosphatidylserine, a maleimidyl-derivatized phospholipid (e.g., N-[4(p-malei-midophenyl)butyryl]phosphatidylethanolamine), dioleylphosphatidylcholine, dipalmitoylphosphatidylglycerol, dimyristoylphosphatidic acid, and a combination thereof. Liposomes have been used to deliver therapeutic agents to cells.

The nanoparticles of the invention can also be "stealth liposomes," which comprise lipids wherein the head group is modified with PEG. This results in extended circulating half life in the subject.

Dendritic polymers (otherwise known as "dendrimers") are uniform polymers, variously referred to in the literature as hyperbranched dendrimers, arborols, fractal polymers and starburst dendrimers, having a central core, an interior dendritic (hyperbranched) structure and an exterior surface with end groups. These polymers differ from the classical linear polymers both in form and function. Dendrimer chemistry constructs macromolecules with tight control of size, shape topology, flexibility and surface groups (e.g., a low-molecular weight PSMA ligand). In what is known as divergent synthesis, these macromolecules start by reacting an initiator core in high-yield iterative reaction sequences to build symmetrical branches radiating from the core with well-defined surface groups. Alternatively, in what is known as convergent synthesis, dendritic wedges are constructed from the periphery inwards towards a focal point and then several dendritic wedges are coupled at the focal points with a polyfunctional core. Dendritic syntheses form concentric layers, known as generations, with each generation doubling the molecular mass and the number of reactive groups at the branch ends so that the end generation dendrimer is a highly pure, uniform monodisperse macromolecule that solubilizes readily over a range of conditions. For the reasons discussed below, dendrimer molecular weights range from 300 to 700,000 daltons and the number of surface groups (e.g., reactive sites for coupling) range significantly.

"Albumin particles" (also referred to as "albumin microspheres") have been reported as carriers of pharmacological or diagnostic agents (see, e.g., U.S. Pat. Nos. 5,439,686; 5,498,421; 5,560,933; 5,665,382; 6,096,331; 6,506,405; 6,537,579; 6,749,868; and 6,753,006; all of which are incorporated herein by reference). Microspheres of albumin have been prepared by either heat denaturation or chemical crosslinking. Heat denatured microspheres are produced from an emulsified mixture (e.g., albumin, the agent to be incorporated, and a suitable oil) at temperatures between 100° C. and 150° C. The microspheres are then washed with a suitable solvent and stored. Leucuta et al. (International Journal of Pharmaceutics 41:213-217 (1988)) describe the method of preparation of heat denatured microspheres.

Small Molecule Targeting Moieties

In yet another set of embodiments, a polymeric conjugate of the present invention includes a targeting moiety, i.e., a moiety able to bind to or otherwise associate with a biological entity, for example, a membrane component, a cell surface receptor, prostate specific membrane antigen, or the like. In the case of the instant invention, the targeting moiety is a low-molecular weight PSMA ligand. The term "bind" or "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules, such as polynucleotides, that are able to bind to or recognize a binding partner (or a limited number of binding partners) to a substantially higher degree than to other, similar biological entities. In one set of embodiments, the targeting moiety has an affinity (as measured via a disassociation constant) of less than about 1 micromolar, at least about 10 micromolar, or at least about 100 micromolar.

In preferred embodiments, the targeting moiety of the invention is a small molecule. In certain embodiments, the term "small molecule" refers to organic compounds, whether naturally-occurring or artificially created (e.g., via chemical synthesis) that have relatively low molecular weight and that are not proteins, polypeptides, or nucleic acids. Small molecules typically have multiple carbon-carbon bonds. In certain embodiments, small molecules are less than about 2000 g/mol in size. In some embodiments, small molecules are less than about 1500 g/mol or less than about 1000 g/mol. In some embodiments, small molecules are less than about 800 g/mol or less than about 500 g/mol.

In particularly preferred embodiments, the small molecule targeting moiety targets prostate cancer tumors, and, in particular, the small molecule targeting moiety is a PSMA peptidase inhibitor. These moieties are also referred to herein as "low-molecular weight PSMA ligands." When compared with expression in normal tissues, expression of prostate specific membrane antigen (PSMA) is at least 10-fold overexpressed in malignant prostate relative to normal tissue, and the level of PSMA expression is further up-regulated as the disease progresses into metastatic phases (Silver et al. 1997, *Clin. Cancer Res.*, 3:81).

In some embodiments, the low-molecular weight PSMA ligand is of the Formulae I, II, III or IV:

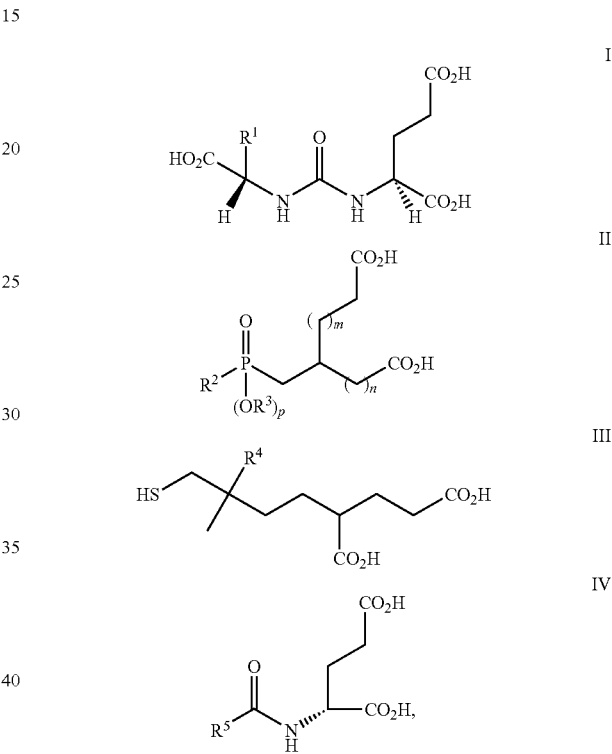

and enantiomers, stereoisomers, rotamers, tautomers, diastereomers, or racemates thereof;

wherein m and n are each, independently, 0, 1, 2 or 3;

p is 0 or 1;

$R^1$, $R^2$, $R^4$ and $R^5$ are each, independently, selected from the group consisting of substituted or unsubstituted alkyl (e.g., $C_{1-10}$-alkyl, $C_{1-6}$-alkyl, or $C_{1-4}$-alkyl), substituted or unsubstituted aryl (e.g., phenyl or pyridinyl), and any combination thereof; and $R^3$ is H or $C_{1-6}$-alkyl (e.g., $CH_3$).

For compounds of Formulae I, II, III and IV, $R^1$, $R^2$, $R^4$ and $R^5$ comprise points of attachment to the nanoparticle, e.g., a polymer that comprises the nanoparticle, e.g., PEG. The point of attachment may be formed by a covalent bond, ionic bond, hydrogen bond, a bond formed by adsorption including chemical adsorption and physical adsorption, a bond formed from van der Waals bonds, or dispersion forces. For example, if $R^1$, $R^2$, $R^4$ or $R^5$ are defined as an aniline or $C_{1-6}$-alkyl-$NH_2$ group, any hydrogen (e.g., an amino hydrogen) of these functional groups could be removed such that the low-molecular weight PSMA ligand is covalently bound to the polymeric matrix (e.g., the PEG-block of the polymeric matrix) of the nanoparticle. As used herein, the term "covalent bond" refers to a bond between two atoms formed by sharing at least one pair of electrons.

In particular embodiments of the Formulae I, II, III or IV, $R^1$, $R^2$, $R^4$ and $R^5$ are each, independently, $C_{1-6}$-alkyl or phenyl, or any combination of $C_{1-6}$-alkyl or phenyl, which are independently substituted one or more times with OH, SH, $NH_2$, or $CO_2H$, and wherein the alkyl group may be interrupted by N(H), S or O. In another embodiment, $R^1$, $R^2$, $R^4$ and $R^5$ are each, independently, $CH_2$-Ph, $(CH_2)_2$—SH, $CH_2$—SH, $(CH_2)_2C(H)(NH_2)CO_2H$, $CH_2C(H)(NH_2)CO_2H$, $CH(NH_2)CH_2CO_2H$, $(CH_2)_2C(H)(SH)CO_2H$, $CH_2$—N(H)-Ph, O—$CH_2$-Ph, or O—$(CH_2)_2$-Ph, wherein each Ph may be independently substituted one or more times with OH, $NH_2$, $CO_2H$ or SH. For these formulae, the $NH_2$, OH or SH groups serve as the point of covalent attachment to the nanoparticle (e.g., —N(H)-PEG, —O-PEG, or —S-PEG).

In still another embodiment, the low-molecular weight PSMA ligand is selected from the group consisting of

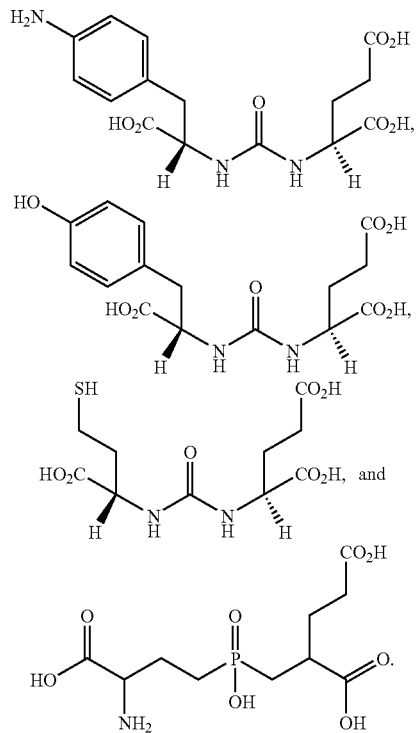

and enantiomers, stereoisomers, rotamers, tautomers, diastereomers, or racemates thereof, and wherein the $NH_2$, OH or SH groups serve as the point of covalent attachment to the nanoparticle (e.g., —N(H)-PEG, —O-PEG, or —S-PEG).

In another embodiment, the low-molecular weight PSMA ligand is selected from the group consisting of

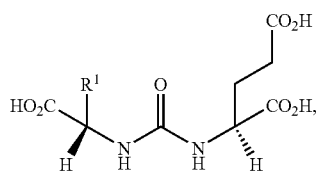

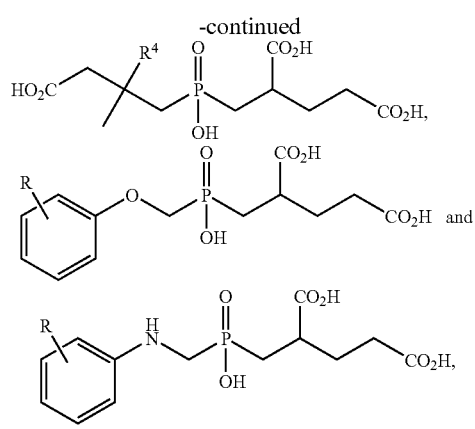

and enantiomers, stereoisomers, rotamers, tautomers, diastereomers, or racemates thereof, wherein R is independently selected from the group consisting of $NH_2$, SH, OH, $CO_2H$, $C_{1-6}$-alkyl that is substituted with $NH_2$, SH, OH or $CO_2H$, and phenyl that is substituted with $NH_2$, SH, OH or $CO_2H$, and wherein R serves as the point of covalent attachment to the nanoparticle (e.g., —N(H)-PEG, —S-PEG, —O-PEG, or $CO_2$-PEG).

In another embodiment, the low-molecular weight PSMA ligand is selected from the group consisting of

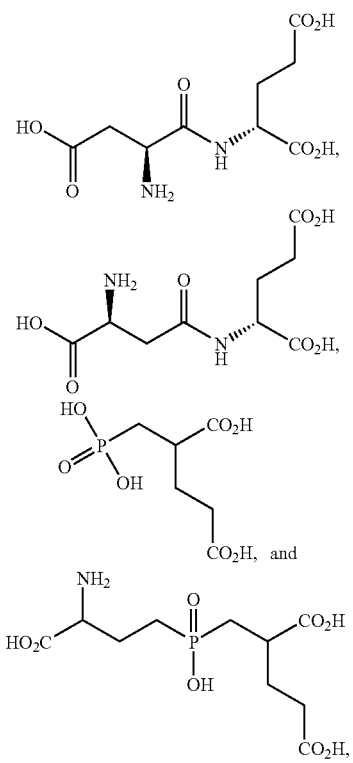

and enantiomers, stereoisomers, rotamers, tautomers, diastereomers, or racemates thereof, wherein the $NH_2$ or $CO_2H$ groups serve as the point of covalent attachment to the nanoparticle (e.g., —N(H)-PEG, or $CO_2$-PEG). These compounds may be further substituted with $NH_2$, SH, OH, $CO_2H$, $C_{1-6}$-alkyl that is substituted with $NH_2$, SH, OH or $CO_2H$, or phenyl that is substituted with $NH_2$, SH, OH or $CO_2H$, wherein these functional groups can also serve as the point of covalent attachment to the nanoparticle.

In another embodiment, the low-molecular weight PSMA ligand is

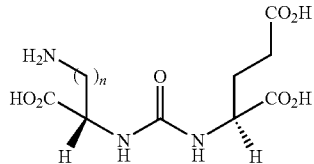

and enantiomers, stereoisomers, rotamers, tautomers, diastereomers, or racemates thereof, wherein n is 1, 2, 3, 4, 5 or 6. For this ligand, the $NH_2$ group serves as the point of covalent attachment to the nanoparticle (e.g., —N(H)-PEG).

In still another embodiment, the low-molecular weight PSMA ligand is

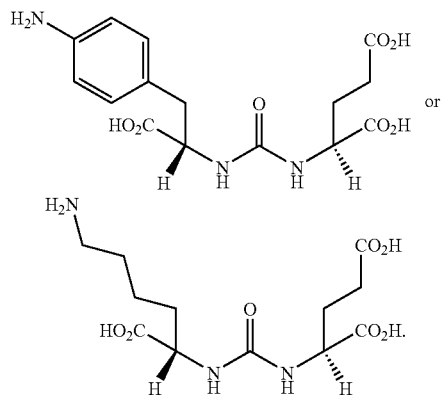

and enantiomers, stereoisomers, rotamers, tautomers, diastereomers, or racemates thereof. Particularly, the butyl-amine compound has the advantage of ease of synthesis, especially because of its lack of a benzene ring. Furthermore, without wishing to be bound by theory, the butyl-amine compound will likely break down into naturally occurring molecules (i.e., lysine and glutamic acid), thereby minimizing toxicity concerns.

For these ligands, the $NH_2$ groups serve as the point of covalent attachment to the nanoparticle (e.g., —N(H)-PEG). Accordingly, the present invention provides the low-molecular weight PSMA ligands shown above, wherein the amine substituents of the compounds are covalently bound to poly(ethylene glycol), e.g., the compounds:

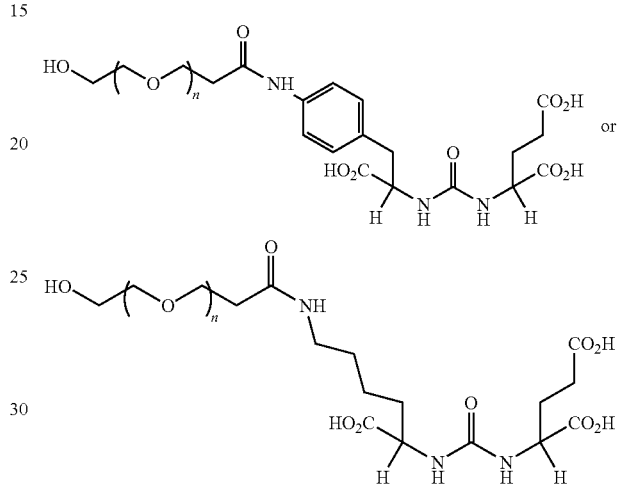

wherein n is 20 to 1720.

The compounds of the invention also include the low-molecular weight PSMA ligands of Formulae I, II, III or IV, wherein the low-molecular weight PSMA ligands are bound to a polymer. Such conjugates include:

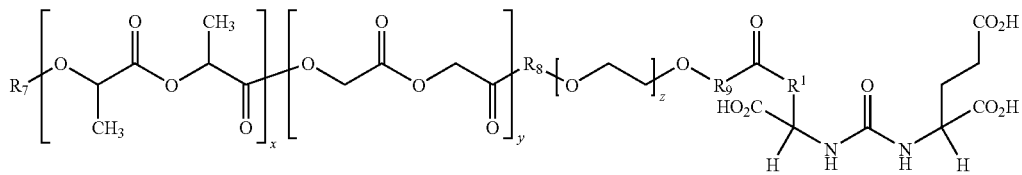

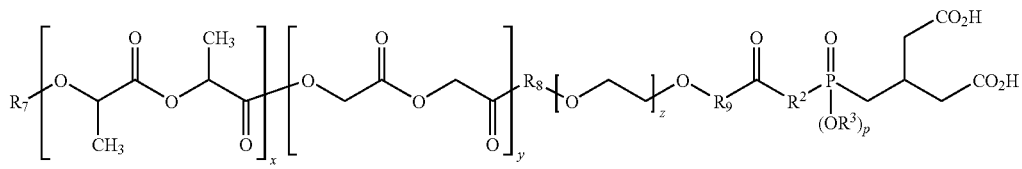

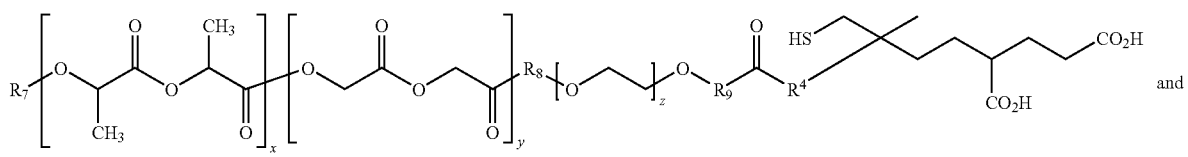

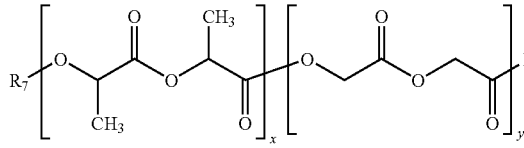 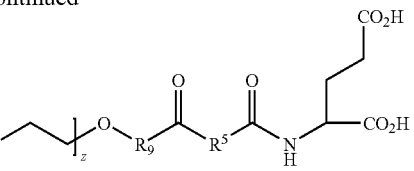

wherein $R_1$, $R_2$, $R_3$, $R_4$ and $R_5$ have the definitions described for Formulae I, II, III or IV, and wherein $R_7$ and $R_9$ are alkyl groups, $R_8$ is an ester or amide linkage, X=0 to 1 mole fraction, Y=0 to 0.5 mole fraction, X+Y=20 to 1720, and Z=25 to 455.

The compounds of the invention also include:

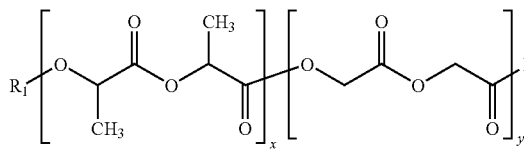 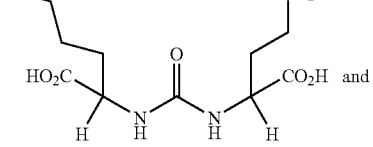

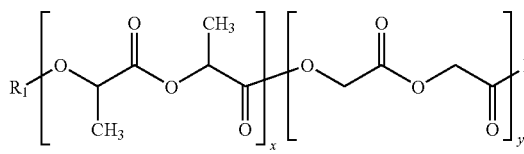 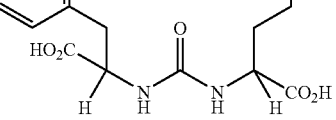

wherein $R_1$ and $R_3$ are alkyl groups, $R_2$ is an ester or amide linkage, X=0 to 1 mole fraction, Y=0 to 0.5 mole fraction, X+Y=20 to 1720, and Z=25 to 455.

Accordingly, the invention provides target-specific stealth nanoparticle comprising a therapeutic agent and any of the polymer/low-molecular weight PSMA ligand conjugates described above.

In some embodiments, the low-molecular weight PSMA ligand is selected from those ligands described in Zhou et al., Nat. Rev. Drug Discov. 4:1015-26 (2005); Humblett et al., Mol. Imaging 4:448-62 (2005); Jayaprakash et al., Chem. Med. Chem. 1:299-302 (2006); Yoo et al., Controlled Release 96: 273-83 (2004); Aggarwal et al., Cancer Res. 66:9171-9177 (2006); and Foss et al., Clin. Cancer Res. 11(11): 4022-4028 (2005) all of which are incorporated herein by reference in their entireties.

In some embodiments, small molecule targeting moieties that may be used to target cells associated with prostate cancer tumors include PSMA peptidase inhibitors such as 2-PMPA, GPI5232, VA-033, phenylalkylphosphonamidates (Jackson et al., 2001, *Curr. Med. Chem.*, 8:949; Bennett et al, 1998, *J. Am. Chem. Soc.*, 120:12139; Jackson et al., 2001, *J. Med. Chem.*, 44:4170; Tsulcarnoto et al, 2002, *Bioorg. Med. Chem. Lett.*, 12:2189; Tang et al., 2003, *Biochem. Biophys. Res. Commun.*, 307:8; Oliver et al., 2003, *Bioorg. Med. Chem.*, 11:4455; and Maung et al., 2004, *Bioorg. Med. Chem.*, 12:4969), and/or analogs and derivatives thereof. In some embodiments, small molecule targeting moieties that may be used to target cells associated with prostate cancer tumors include thiol and indole thiol derivatives, such as 2-MPPA and 3-(2-mercaptoethyl)-1H-indole-2-carboxylic acid derivatives (Majer et al, 2003, *J. Med. Chem.*, 46:1989; and U.S. Patent Publication 2005/0080128). In some embodiments, small molecule targeting moieties that may be used to target cells associated with prostate cancer tumors include hydroxamate derivatives (Stoermer et al, 2003, *Bioorg. Med. Chem. Lett.*, 13:2097). In some embodiments, small molecule targeting moieties that may be used to target cells associated with prostate cancer tumors include PBDA- and urea-based inhibitors, such as ZJ 43, ZJ 11, ZJ 17, ZJ 38 (Nan et al. 2000, *J. Med. Chem.*, 43:772; and Kozikowski et al, 2004, *J. Med. Chem.*, 47:1729), and/or and analogs and derivatives thereof. In some embodiments, small molecule targeting moieties that may be used to target cells associated with prostate cancer tumors include androgen receptor targeting agents (ARTAs), such as those described in U.S. Pat. Nos. 7,026,500; 7,022,870; 6,998,500; 6,995,284; 6,838,484; 6,569,896; 6,492,554; and in U.S. Patent Publications 2006/0287547; 2006/0276540; 2006/0258628; 2006/0241180; 2006/0183931; 2006/0035966; 2006/0009529; 2006/0004042; 2005/0033074; 2004/0260108; 2004/0260092; 2004/0167103; 2004/0147550; 2004/0147489; 2004/0087810; 2004/0067979; 2004/0052727; 2004/0029913; 2004/0014975; 2003/0232792; 2003/0232013; 2003/0225040; 2003/0162761; 2004/0087810; 2003/0022868; 2002/0173495; 2002/0099096; 2002/0099036.

In some embodiments, small molecule targeting moieties that may be used to target cells associated with prostate cancer tumors include polyamines, such as putrescine, spermine, and spermidine (U.S. Patent Publications 2005/0233948 and 2003/0035804).

In some embodiments, the low molecular weight PSMA ligand is an inhibitor of the enzyme glutamate carboxylase II (GCPII), also known as NAAG Peptidase or NAALADase. Accordingly, one could assay GCPII or NAALADase inhibitory activity as a basis to design/identify low molecular weight small molecules that bind PSMA. As such, the present invention is related to stealth nanoparticles with low molecular weight PSMA ligands that can be used for the treatment of cancers associated with GCPII activity.

Methods to screen for low molecular weight molecules capable of binding specifically to the cell surface proteins PSMA or GCPII are well known in the art. In a non-limiting example, candidate low molecular weight molecules can be labeled either radioactively (see Foss et al., Clin Cancer Res, 2005, 11, 4022-4028) or fluorescently (Humblet et al., Molecular Imaging, 2005, 4, 448-462). A standard laboratory cell line, e.g., HeLa cells, that do not normally express PMSA (control cells) can be transfected with a transgene encoding the PMSA protein such that PMSA is expressed on the cell surface of these transfected cells. The ability of the low molecular weight, labeled molecules to bind to the cells ectopically expressing PMSA but not to control cells can be determined in vitro using standard, art recognized means such scintillation counting or Fluorescence Activated Cell sorting (FACS) analysis. Low molecular weight molecules that bind to cells expressing PMSA but not to the control cells would be considered specific for PMSA. The binding and uptake of nanoparticles can be assessed with assays using LNCap cells, which express PSMA (see, e.g., Example 4 herein).

The molecules disclosed in the patents, patent applications, and non-patent references cited herein can be further substituted with a functional group that can be reacted with a polymer of the invention (e.g., PEG) in order to produce a polymer conjugated to a targeting moiety. The functional groups include any moiety that can be used to create a covalent bond with a polymer (e.g., PEG), such as amino, hydroxy, and thio. In a particular embodiment, the small molecules can be substituted with $NH_2$, SH or OH, which are either bound directly to the small molecule, or bound to the small molecule via an additional group, e.g., alkyl or phenyl. In a non-limiting example, the small molecules disclosed in the patents, patent applications, and non-patent references cited herein may be bound to aniline, alkyl-$NH_2$ (e.g., $(CH_2)_{1-6}NH_2$), or alkyl-SH (e.g., $(CH_2)_{1-6}NH_2$), wherein the $NH_2$ and SH groups may be reacted with a polymer (e.g., PEG), to form a covalent bond with that polymer, i.e., to form a polymeric conjugate.

A polymeric conjugate of the present invention may be formed using any suitable conjugation technique. For instance, two compounds such as a targeting moiety and a biocompatible polymer, a biocompatible polymer and a poly(ethylene glycol), etc., may be conjugated together using techniques such as EDC-NHS chemistry (1-ethyl-3-(3-dimethylaminopropyl) carbodiimide hydrochloride and N-hydroxysuccinimide) or a reaction involving a maleimide or a carboxylic acid, which can be conjugated to one end of a thiol, an amine, or a similarly functionalized polyether. The conjugation of such polymers, for instance, the conjugation of a poly(ester) and a poly(ether) to form a poly(ester-ether), can be performed in an organic solvent, such as, but not limited to, dichloromethane, acetonitrile, chloroform, dimethylformamide, tetrahydrofuran, acetone, or the like. Specific reaction conditions can be determined by those of ordinary skill in the art using no more than routine experimentation.

In another set of embodiments, a conjugation reaction may be performed by reacting a polymer that comprises a carboxylic acid functional group (e.g., a poly(ester-ether) compound) with a polymer or other moiety (such as a targeting moiety) comprising an amine. For instance, a targeting moiety, such as a low-molecular weight PSMA ligand, may be reacted with an amine to form an amine-containing moiety, which can then be conjugated to the carboxylic acid of the polymer. Such a reaction may occur as a single-step reaction, i.e., the conjugation is performed without using intermediates such as N-hydroxysuccinimide or a maleimide. The conjugation reaction between the amine-containing moiety and the carboxylic acid-terminated polymer (such as a poly(ester-ether) compound) may be achieved, in one set of embodiments, by adding the amine-containing moiety, solubilized in an organic solvent such as (but not limited to) dichloromethane, acetonitrile, chloroform, tetrahydrofuran, acetone, formamide, dimethylformamide, pyridines, dioxane, or dimethysulfoxide, to a solution containing the carboxylic acid-terminated polymer. The carboxylic acid-terminated polymer may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer may occur spontaneously, in some cases. Unconjugated reactants may be washed away after such reactions, and the polymer may be precipitated in solvents such as, for instance, ethyl ether, hexane, methanol, or ethanol.

As a specific example, a low-molecular weight PSMA ligand may be prepared as a targeting moiety in a particle as follows. Carboxylic acid modified poly(lactide-co-glycolide) (PLGA-COOH) may be conjugated to an amine-modified heterobifunctional poly(ethylene glycol) ($NH_2$-PEG-COOH) to form a copolymer of PLGA-PEG-COOH. By using an amine-modified low-molecular weight PSMA ligand ($NH_2$-Lig), a triblock polymer of PLGA-PEG-Lig may be formed by conjugating the carboxylic acid end of the PEG to the amine functional group on the ligand. The multiblock polymer can then be used, for instance, as discussed below, e.g., for therapeutic applications.

Another aspect of the invention is directed to particles that include polymer conjugates such as the ones described above. The particles may have a substantially spherical (i.e., the particles generally appear to be spherical), or non-spherical configuration. For instance, the particles, upon swelling or shrinkage, may adopt a non-spherical configuration. In some cases, the particles may include polymeric blends. For instance, a polymer blend may be formed that includes a first polymer comprising a targeting moiety (i.e., a low-molecular weight PSMA ligand) and a biocompatible polymer, and a second polymer comprising a biocompatible polymer but not comprising the targeting moiety. By controlling the ratio of the first and second polymers in the final polymer, the concentration and location of targeting moiety in the final polymer may be readily controlled to any suitable degree.

As used herein, the term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl(alicyclic) groups (cyclopropyl, cyclopentyl, cyclohexyl, cycloheptyl, cyclooctyl), alkyl substituted cycloalkyl groups, and cycloalkyl substituted alkyl groups. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl.

The term alkyl further includes alkyl groups which can further include oxygen, nitrogen, sulfur or phosphorous atoms replacing one or more carbons of the hydrocarbon backbone. In an embodiment, a straight chain or branched chain alkyl has 10 or fewer carbon atoms in its backbone (e.g., $C_1$-$C_{10}$ for straight chain, $C_3$-$C_{10}$ for branched chain), and more preferably 6 or fewer carbons. Likewise, preferred cycloalkyls have from 4-7 carbon atoms in their ring structure, and more preferably have 5 or 6 carbons in the ring structure.

Moreover, alkyl (e.g., methyl, ethyl, propyl, butyl, pentyl, hexyl, etc.) includes both "unsubstituted alkyl" and "substituted alkyl", the latter of which refers to alkyl moieties having substituents replacing a hydrogen on one or more carbons of the hydrocarbon backbone, which allow the molecule to perform its intended function. The term "substituted" is intended to describe moieties having substituents replacing a hydrogen on one or more atoms, e.g. C, O or N, of a molecule. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclic, alkylaryl, morpholino, phenol, benzyl, phenyl, piperizine, cyclopentane, cyclohexane, pyridine, 5H-tetrazole, triazole, piperidine, or an aromatic or heteroaromatic moiety.

Further examples of substituents of the invention, which are not intended to be limiting, include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., —$NH_2$), $(CR'R'')_{0-3}CN$ (e.g., —CN), —$NO_2$, halogen (e.g., —F, —Cl, —Br, or —I), $(CR'R'')_{0-3}C(halogen)_3$ (e.g., —$CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., —$SO_3H$, —$OSO_3H$), $(CR'R'')_{0-3}O(CR'R'')_{0-3}H$ (e.g., —$CH_2OCH_3$ and —$OCH_3$), $(CR'R'')_{0-3}S(CR'R'')_{0-3}H$ (e.g., —SH and —$SCH_3$), $(CR'R'')_{0-3}OH$ (e.g., —OH), $(CR'R'')_{0-3}COR'$, $(CR'R'')_{0-3}$ (substituted or unsubstituted phenyl), $(CR'R'')_{0-3}(C_3$-$C_8$ cycloalkyl), $(CR'R'')_{0-3}CO_2R'$ (e.g., —$CO_2H$), or $(CR'R'')_{0-3}OR'$ group, or the side chain of any naturally occurring amino acid; wherein R' and R'' are each independently hydrogen, a $C_1$-$C_5$ alkyl, $C_2$-$C_5$ alkenyl, $C_2$-$C_5$ alkynyl, or aryl group. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, oxime, thiol, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. In certain embodiments, a carbonyl moiety (C=O) can be further derivatized with an oxime moiety, e.g., an aldehyde moiety can be derivatized as its oxime (—C=N—OH) analog. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (i.e., benzyl)).

The term "aryl" includes groups, including 5- and 6-membered single-ring aromatic groups that can include from zero to four heteroatoms, for example, phenyl, pyrrole, furan, thiophene, thiazole, isothiaozole, imidazole, triazole, tetrazole, pyrazole, oxazole, isoxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, anthryl, phenanthryl, napthridine, indole, benzofuran, purine, benzofuran, deazapurine, or indolizine. Those aryl groups having heteroatoms in the ring structure can also be referred to as "aryl heterocycles", "heterocycles," "heteroaryls" or "heteroaromatics." The aromatic ring can be substituted at one or more ring positions with such substituents as described above, as for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

Additionally, the phrase "any combination thereof" implies that any number of the listed functional groups and molecules can be combined to create a larger molecular architecture. For example, the terms "alkyl" and "aryl" can be combined to form —$CH_2Ph$, or a -$PhCH_3$ (touyl) group. Likewise, the phrase "any combination of $C_{1-6}$-alkyl or phenyl, which are independently substituted one or more times with OH, SH, $NH_2$, or $CO_2H$" represent a —$(CH_2)_3$-analine structure, or a -Ph-$(CH_2)_3$—$NH_2$ substitutent. It is to be understood that when combining functional groups and molecules to create a larger molecular architecture, hydrogens can be removed or added, as required to satisfy the valence of each atom.

Preparation of Target-Specific Stealth Nanoparticles

Another aspect of the invention is directed to systems and methods of producing such target-specific stealth nanoparticles. In some embodiments, a solution containing a polymer is contacted with a liquid, such as an immiscible liquid, to form nanoparticles containing the polymeric conjugate.

As mentioned, one aspect of the invention is directed to a method of developing nanoparticles with desired properties, such as desired chemical, biological, or physical properties. In one set of embodiments, the method includes producing libraries of nanoparticles having highly controlled properties, which can be formed by mixing together two or more polymers in different ratios. By mixing together two or more different polymers (e.g., copolymers, e.g., block copolymers) in different ratios and producing particles from the polymers (e.g., copolymers, e.g., block copolymers), particles having highly controlled properties may be formed. For example, one polymer (e.g., copolymer, e.g., block copolymer) may include a low-molecular weight PSMA ligand, while another polymer (e.g., copolymer, e.g., block copolymer) may be chosen for its biocompatibility and/or its ability to control immunogenicity of the resultant particle.

In one set of embodiments, the particles are formed by providing a solution comprising one or more polymers, and contacting the solution with a polymer nonsolvent to produce the particle. The solution may be miscible or immiscible with the polymer nonsolvent. For example, a water-miscible liquid such as acetonitrile may contain the polymers, and particles are formed as the acetonitrile is contacted with water, a polymer nonsolvent, e.g., by pouring the acetonitrile into the water at a controlled rate. The polymer contained within the solution, upon contact with the polymer nonsolvent, may then precipitate to form particles such as nanoparticles. Two liquids are said to be "immiscible" or not miscible, with each other when one is not soluble in the other to a level of at least 10% by weight at ambient temperature and pressure. Typically, an organic solution (e.g., dichloromethane, acetonitrile, chloroform, tetrahydrofuran, acetone, formamide, dimethylformamide, pyridines, dioxane, dimethysulfoxide, etc.) and an aqueous liquid (e.g., water, or water containing dissolved salts or other species, cell or biological media, ethanol, etc.) are immiscible with respect to each other. For example, the first solution may be poured into the second solution (at a suitable rate or speed). In some cases, particles such as nanoparticles may be formed as the first solution contacts the immiscible second liquid, e.g., precipitation of the polymer upon contact causes the polymer to form nanoparticles while the first solution poured into the second liquid, and in some cases, for example, when the rate of introduction is carefully controlled and kept at a relatively slow rate, nanoparticles may form. The control of such particle formation can be readily optimized by one of ordinary skill in the art using only routine experimentation.

By creating a library of such particles, particles having any desirable properties may be identified. For example, properties such as surface functionality, surface charge, size, zeta ($\zeta$) potential, hydrophobicity, ability to control immunogenicity, and the like, may be highly controlled. For instance, a library of particles may be synthesized, and screened to identify the particles having a particular ratio of polymers that allows the particles to have a specific density of moieties (e.g., low-molecular weight PSMA ligands) present on the surface of the particle. This allows particles having one or more specific properties to be prepared, for example, a specific size and a specific surface density of moieties, without an undue degree of effort. Accordingly, certain embodiments of the invention are directed to screening techniques using such libraries, as well as any particles identified using such libraries. In addition, identification may occur by any suitable method. For instance, the identification may be direct or indirect, or proceed quantitatively or qualitatively.

In some embodiments, already-formed nanoparticles are functionalized with a targeting moiety using procedures analogous to those described for producing ligand-functionalized polymeric conjugates. As a specific, non-limiting example, this embodiment is exemplified schematically in FIG. 1A. In this figure, a first copolymer (PLGA-PEG, poly (lactide-co-glycolide) and poly(ethylene glycol)) is mixed with a therapeutic agent to form particles. The particles are then associated with a low-molecular weight PSMA ligand to form nanoparticles that can be used for the treatment of cancer. The particles can be associated with varying amounts of low-molecular weight PSMA ligands in order to control the PSMA ligand surface density of the nanoparticle, thereby altering the therapeutic characteristics of the nanoparticle. Furthermore, for example, by controlling parameters such as PLGA molecular weight, the molecular weight of PEG, and the nanoparticle surface charge, very precisely controlled particles may be obtained using this method of preparation.

As a specific, non-limiting example, another embodiment is shown schematically in FIG. 1B. In this figure, a first copolymer (PLGA-PEG) is conjugated to a low-molecular weight PSMA ligand (PSMALig) to form a PLGA-PEG-PSMALig polymer. This ligand-bound polymer is mixed with a second, non-functionalized polymer (PLGA-PEG in this example) at varying ratios to form a series of particles having different properties, for example, different surface densities of PSMA ligand as shown in this example. For example, by controlling parameters such as PLGA molecular weight, the molecular weight of PEG, the PSMA ligand surface density, and the nanoparticle surface charge, very precisely controlled particles may be obtained using this method of preparation. As shown in FIG. 1B, the resulting nanoparticle can also include a therapeutic agent.

In another embodiment, the invention provides a method of preparing a stealth nanoparticle wherein the nanoparticle has a ratio of ligand-bound polymer to non-functionalized polymer effective for the treatment of prostate cancer, wherein the hydrophilic, ligand-bound polymer is conjugated to a lipid that will self assemble with the hydrophobic polymer, such that the hydrophobic and hydrophilic polymers that constitute the nanoparticle are not covalently bound. "Self-assembly" refers to a process of spontaneous assembly of a higher order structure that relies on the natural attraction of the components of the higher order structure (e.g., molecules) for each other. It typically occurs through random movements of the molecules and formation of bonds based on size, shape, composition, or chemical properties. For example, such a method comprises providing a first polymer that is reacted with a lipid, to form a polymer/lipid conjugate. The polymer/lipid conjugate is then reacted with the low-molecular weight PSMA ligand to prepare a ligand-bound polymer/lipid conjugate; and mixing the ligand-bound polymer/lipid conjugate with a second, non-functionalized polymer, and the therapeutic agent; such that the stealth nanoparticle is formed. In certain embodiments, the first polymer is PEG, such that a lipid-terminated PEG is formed. In one embodiment, the lipid is of the Formula V, e.g., 2 distearoyl-sn-glycero-3-phosphoethanolamine (DSPE), and salts thereof, e.g., the sodium salt. The lipid-terminated PEG can then, for example, be mixed with PLGA to form a nanoparticle.

Libraries of such particles may also be formed. For example, by varying the ratios of the two (or more) polymers within the particle, these libraries can be useful for screening tests, high-throughput assays, or the like. Entities within the library may vary by properties such as those described above, and in some cases, more than one property of the particles may be varied within the library. Accordingly, one embodiment of the invention is directed to a library of nanoparticles having different ratios of polymers with differing properties. The library may include any suitable ratio(s) of the polymers.

In some cases, a population of particles may be present. For example, a population of particles may include at least 20 particles, at least 50 particles, at least 100 particles, at least 300 particles, at least 1,000 particles, at least 3,000 particles, or at least 10,000 particles. Various embodiments of the present invention are directed to such populations of particles. For instance, in some embodiments, the particles may each be substantially the same shape and/or size ("monodisperse"). For example, the particles may have a distribution of characteristic dimensions such that no more than about 5% or about 10% of the particles have a characteristic dimension greater than about 10% greater than the average characteristic dimension of the particles, and in some cases, such that no more than about 8%, about 5%, about 3%, about 1%, about 0.3%, about 0.1%, about 0.03%, or about 0.01% have a characteristic dimension greater than about 10% greater man the average characteristic dimension of the particles. In some cases, no more than about 5% of the particles have a characteristic dimension greater than about 5%, about 3%, about 1%, about 0.3%, about 0.1%, about 0.03%, or about 0.01% greater than the average characteristic dimension of the particles.

More generally, the polymers chosen to be used to create the library of particles may be any of a wide variety of polymers, such as described herein. Generally, two, three, four, or more polymers are mixed, in a wide range of ratios (e.g., each ranging from 0% to 100%), to form particles such as nanoparticles having different ratios of each of the polymers. The two or more polymers may be distinguishable in some fashion, e.g., having different polymeric groups, having the same polymeric groups but with different molecular weights, having some polymeric groups in common but having others that are different (e.g., one may have a polymeric group that the other does not have), having the same polymeric groups but in different orders, etc. The library of particles may have any number of members, for example, the library may have 2, 3, 5, 10, 30, 100, 300, 1000, 3000, 10,000, 30,000, 100,000, etc. members, which can be identified in some fashion. In some cases, the library may exist contemporaneously; for example, the library may be contained in one or more microtiter plates, vials, etc., or in some embodiments, the library may have include members created at different times.

The library of particles can then be screened in some fashion to identify those particles having one or more desired properties, for example, surface functionality, surface charge, size, zeta (ζ) potential, hydrophobicity, ability to control immunogenicity, and the like. One or more of the macromolecules within the particles may include one or more polymers chosen to be biocompatible or biodegradable, one or more polymers chosen to reduce immunogenicity, and/or one or more low-molecular weight PSMA ligands. The macromolecules within the library may comprise some or all of these polymers, in any suitable combination (including, but not limited to, combinations in which a first polymer comprises a low-molecular weight PSMA ligand and a second polymer does not contain any of these species).

As a specific example, in one embodiment, the particles may include a first macromolecule comprising a biocompatible polymer, and a low-molecular weight PSMA ligand, and a second macromolecule comprising a biocompatible polymer, which may or may not be the same as that of the first macromolecule. As another example, a first macromolecule may be a block copolymer comprising a biocompatible hydrophobic polymer, a biocompatible hydrophilic polymer, and a low-molecular weight PSMA ligand; and a second macromolecule distinguishable from the first macromolecule in some fashion. For instance, the second macromolecule may comprise the same (or a different) biocompatible hydrophobic polymer and the same (or a different) biocompatible hydrophilic polymer, but a different low-molecular weight PSMA ligand (or no ligand at all) than the first macromolecule.

The nanoparticle of the invention may also be comprised of, as another example, a first macromolecule comprising a biocompatible hydrophobic polymer, a biocompatible hydrophilic polymer, and a low-molecular weight PSMA ligand, and a second macromolecule that is distinguishable from the first macromolecule. For instance, the second macromolecule may contain none of the polymers of the first macromolecule, the second macromolecule may contain one or more polymers of the first macromolecule and one or more polymers not present in the first macromolecule, the second macromolecule may lack one or more of the polymers of the first macromolecule, the second macromolecule may contain all of the polymers of the first macromolecule, but in a different order and/or with one or more of the polymers having different molecular weights, etc.

As yet another example, the first macromolecule may comprise a biocompatible hydrophobic polymer, a biocompatible hydrophilic polymer, and a low-molecular weight PSMA ligand, and the second macromolecule may comprise the biocompatible hydrophobic polymer and the biocompatible hydrophilic polymer, and be distinguishable from the first macromolecule in some fashion. As still another example, the first macromolecule may comprise a biocompatible hydrophobic polymer and a biocompatible hydrophilic polymer, and the second macromolecule may comprise the biocompatible hydrophobic polymer and a low-molecular weight PSMA ligand, where the second macromolecule is distinguishable from the first macromolecule in some fashion.

The nanoparticles described above may also contain therapeutic agents. Examples of therapeutic agents include, but are not limited to, a chemotherapeutic agent, a radioactive agent, a nucleic acid-based agent, a lipid-based agent, a carbohydrate based agent, a natural small molecule, or a synthetic small molecule.

The polymers or macromolecules may then be formed into a particle, using techniques such as those discussed in detail below. The geometry formed by the particle from the polymer or macromolecule may depend on factors such as the polymers that form the particle.

FIG. 2 illustrates that libraries can be produced using polymers such as those described above. For example, in FIG. 2, polymeric particles comprising a first macromolecule comprising a biocompatible hydrophobic polymer, a biocompatible hydrophilic polymer, and a low-molecular weight PSMA ligand, and a second macromolecule that comprises a biocompatible hydrophobic polymer and a biocompatible hydrophilic polymer may be used to create a library of particles having different ratios of the first and second macromolecules.

Such a library may be useful in achieving particles having any number of desirable properties, for instance properties such as surface functionality, surface charge, size, zeta (ζ) potential, hydrophobicity, ability to control immunogenicity, or the like. In FIG. 2, different ratios of the first and second macromolecules (including ratios where one of the macromolecules is absent) are combined to produce particles that form the basis of the library.

For instance, as shown in FIG. 2, as the amount of the first macromolecule is increased, relative to the second macromolecule, the amount of moiety (e.g., low-molecular weight PSMA ligand) present on the surface of the particle may be increased. Thus, any suitable concentration of moiety on the surface may be achieved simply by controlling the ratio of the first and second macromolecules in the particles. Accordingly, such a library of particles may be useful in selecting or identifying particles having a particular functionality.

Figure 3:
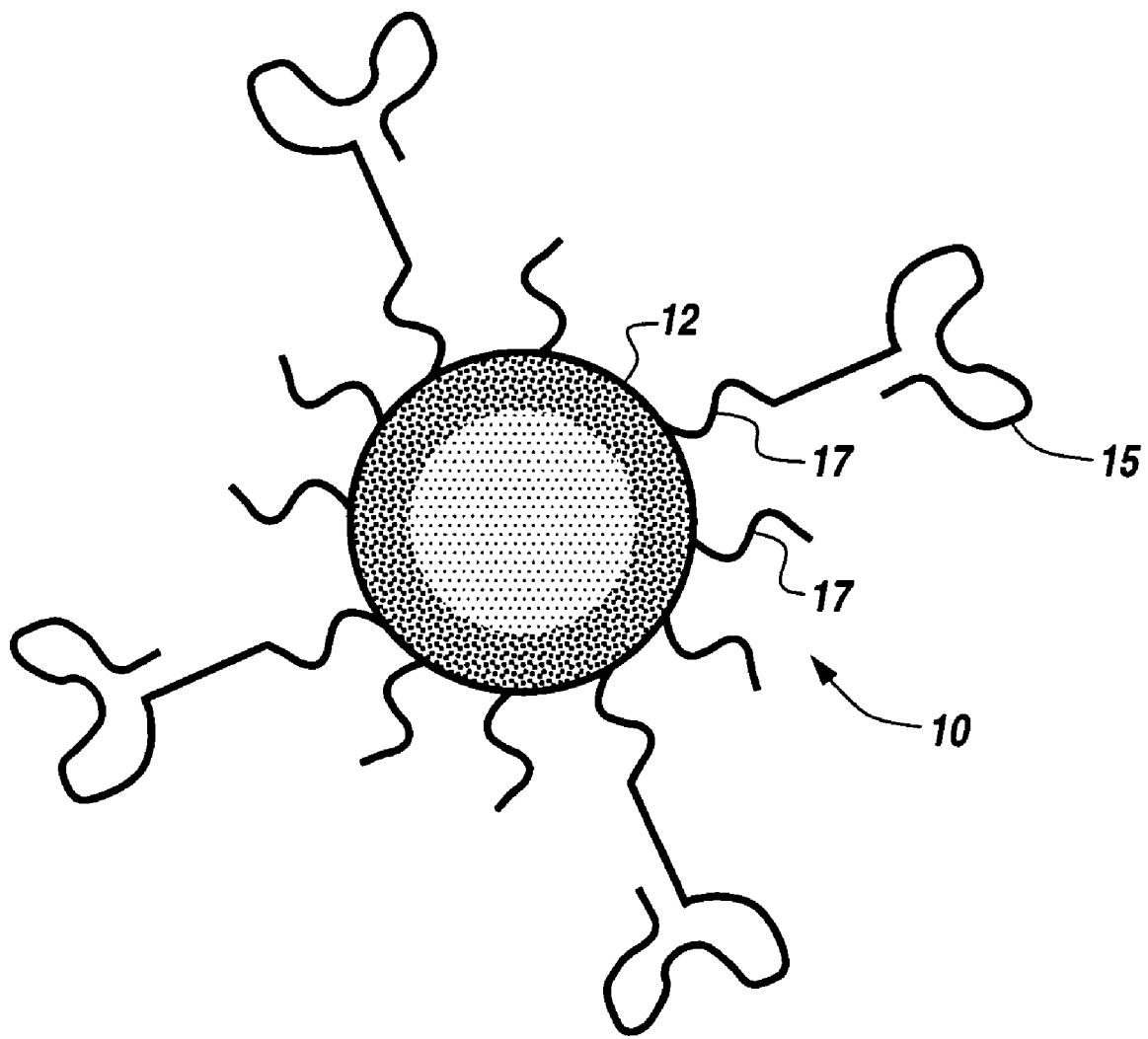
FIG. 3 is a representative schematic of a nanoparticle of the invention.

As specific examples, in some embodiments of the present invention, the library includes particles comprising polymeric conjugates of a biocompatible polymer and a low-molecular weight PSMA ligand, as discussed herein. Referring now to FIG. 3, one such particle is shown as a non-limiting example. In this figure, a polymeric conjugate of the invention is used to form a particle 10. The polymer forming particle 10 includes a low-molecular weight PSMA ligand 15, present on the surface of the particle, and a biocompatible portion 17. In some cases, as shown here, targeting moiety 15 may be conjugated to biocompatible portion 17. However, not all of biocompatible portion 17 is shown conjugated to targeting moiety 15. For instance, in some cases, particles such as particle 10 may be formed using a first polymer comprising biocompatible portion 17 and low-molecular weight PSMA ligand 15, and a second polymer comprising biocompatible portion 17 but not targeting moiety 15. By controlling the ratio of the first and second polymers, particles having different properties may be formed, and in some cases, libraries of such particles may be formed. In addition, contained within the center of particle 10 is drug 12. In some cases, drug 12 may be contained within the particle due to hydrophobic effects. For instance, the interior of the particle may be relatively hydrophobic with respect to the surface of the particle, and the drug may be a hydrophobic drug that associates with the relatively hydrophobic center of the particle. In one embodiment, the therapeutic agent is associated with the surface of, encapsulated within, surrounded by, or dispersed throughout the nanoparticle. In another embodiment, the therapeutic agent is encapsulated within the hydrophobic core of the nanoparticle.

As a specific example, particle 10 may contain polymers including a relatively hydrophobic biocompatible polymer and a relatively hydrophilic targeting moiety 15, such that, during particle formation, a greater concentration of the hydrophilic targeting moiety is exposed on the surface and a greater concentration of the hydrophobic biocompatible polymer is present within the interior of the particle.

In some embodiments, the biocompatible polymer is a hydrophobic polymer. Non-limiting examples of biocompatible polymers include polylactide, polyglycolide, and/or poly(lactide-co-glycolide).

In one embodiment, the invention comprises a nanoparticle comprising 1) a polymeric matrix; 2) an amphiphilic compound or layer that surrounds or is dispersed within the polymeric matrix forming a continuous or discontinuous shell for the particle; 3) a stealth polymer, and 4) a covalently attached low molecular weight PSMA ligand. An amphiphilic layer can reduce water penetration into the nanoparticle, thereby enhancing drug encapsulation efficiency and slowing drug release. Further, these amphipilic layer protected nanoparticles can provide therapeutic advantages by releasing the encapsulated drug and polymer at appropriate times.

As used herein, the term "amphiphilic" refers to a property where a molecule has both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. For purposes of the invention, the amphiphilic compound can be, but is not limited to, one or a plurality of the following: naturally derived lipids, surfactants, or synthesized compounds with both hydrophilic and hydrophobic moieties.

Specific examples of amphiphilic compounds include, but are not limited to, phospholipids, such as 1,2 distearoyl-sn-glycero-3-phosphoethanolamine (DSPE), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), and dilignoceroylphatidylcholine (DLPC), incorporated at a ratio of between 0.01-60 (weight lipid/w polymer), most preferably between 0.1-30 (weight lipid/w polymer). Phospholipids which may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and $\beta$-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophosphoethanolamine. Synthetic phospholipids with asymmetric acyl chains (e.g., with one acyl chain of 6 carbons and another acyl chain of 12 carbons) may also be used.

In a particular embodiment, an amphiphilic component that can be used to form an amphiphilic layer is lecithin, and, in particular, phosphatidylcholine. Lecithin is an amphiphilic lipid and, as such, forms a phospholipid bilayer having the hydrophilic (polar) heads facing their surroundings, which are oftentimes aqueous, and the hydrophobic tails facing each other. Lecithin has an advantage of being a natural lipid that is available from, e.g., soybean, and already has FDA approval for use in other delivery devices. In addition, a mixture of lipids such as lethicin is more advantageous than one single pure lipid.

In certain embodiments of the invention, the amphiphilic layer of the nanoparticle, e.g., the layer of lecithin, is a monolayer, meaning the layer is not a phospholipid bilayer, but exists as a single continuous or discontinuous layer around, or within, the nanoparticle. The amphiphilic layer is "associated with" the nanoparticle of the invention, meaning it is positioned in some proximity to the polymeric matrix, such as surrounding the outside of the polymeric shell, or dispersed within the polymers that make up the nanoparticle.

Thus, in one embodiment, the invention provides a target specific nanoparticle comprising 1) PLGA; 2) PEG; 3) an amphiphilic compound or layer (e.g., lecithin) that surrounds or is dispersed within the PLGA/PEG matrix forming a continuous or discontinuous shell for the particle; and 4) a covalently attached low molecular weight PSMA ligand. In one embodiment, the PLGA and PEG are copolymers, and the low molecular weight PSMA ligand is covalently bound to PEG. In another embodiment, the PEG is bound to DSPE, which self assembles with PLGA, and the low molecular weight PSMA ligand is covalently bound to PEG. In another embodiment, the ratio of amphiphilic compound to polymer is between 14:1 and 34:1, by weight.

In another embodiment, the invention comprises a nanoparticle comprising 1) a polymeric matrix comprising a biodegradable polymer; 2) an amphiphilic compound or layer that surrounds or is dispersed within the polymeric matrix forming a continuous or discontinuous shell for the particle; 3) a stealth polymer, and 4) a covalently attached low molecular weight PSMA ligand, wherein the nanoparticle diameter is between 40-80 nm and wherein the ratio of amphiphilic compound to polymer is between 14:1 and 34:1, by weight. In another embodiment, the invention comprises a nanoparticle comprising 1) a polymeric matrix comprising a biodegradable polymer; 2) lecithin; 3) a stealth polymer, and 4) a covalently attached low molecular weight PSMA ligand. In another embodiment, the invention comprises a nanoparticle comprising 1) a polymeric matrix comprising a biodegradable polymer; 2) lecithin; 3) a stealth polymer, and 4) a covalently attached low molecular weight PSMA ligand, wherein the nanoparticle diameter is between 40-80 nm and wherein the ratio of lecithin to polymer is between 14:1 and 34:1 by weight. In another embodiment, the invention comprises a nanoparticle comprising 1) a polymeric matrix comprising a biodegradable polymer; 2) a mixture of two or more amphiphilic compounds selected from phosphatidyl choline, phosphatidyl inositol, phosphatidyl ethanolamine, and phosphatidic acid; 3) a stealth polymer, and 4) a covalently attached low molecular weight PSMA ligand. In further embodiment, the invention comprises a nanoparticle comprising 1) a polymeric matrix comprising a biodegradable polymer; 2) a mixture of three or more amphiphilic compounds selected from phosphatidyl choline, phosphatidyl inositol, phosphatidyl ethanolamine, and phosphatidic acid; 3) a stealth polymer, and 4) a covalently attached low molecular weight PSMA ligand. In a still further embodiment, the invention comprises a nanoparticle comprising 1) a polymeric matrix comprising a biodegradable polymer; 2) an amphiphilic compound or layer that surrounds or is dispersed within the polymeric matrix forming a continuous or discontinuous shell for the particle; 3) polyethylene glycol, and 4) a covalently attached low molecular weight PSMA ligand. In another embodiment, the invention comprises a nanoparticle comprising 1) a polymeric matrix comprising a biodegradable polymer; 2) lecithin; 3) polyethylene glycol, and 4) a covalently attached low molecular weight PSMA ligand. In another embodiment, the invention comprises a nanoparticle comprising 1) a polymeric matrix comprising a biodegradable polymer; 2) a mixture of two or more amphiphilic compounds selected from phosphatidyl choline, phosphatidyl inositol, phosphatidyl ethanolamine, and phosphatidic acid; 3) polyethylene glycol, and 4) a covalently attached low molecular weight PSMA ligand. In one embodiment, the invention comprises a nanoparticle comprising 1) a polymeric matrix comprising a biodegradable polymer; 2) lecithin; 3) polyethylene glycol, and 4) a covalently attached low molecular weight PSMA ligand, wherein the nanoparticle diameter is between 40-80 nm and wherein the ratio of lecithin to polymer is between 14:1 and 34:1 by weight. In certain embodiments, the biodegradable polymer is PLGA. In other embodiments, the stealth polymer is PEG.

Therapeutic Agents

According to the present invention, any agents ("payload"), including, for example, therapeutic agents (e.g. anticancer agents), diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.) may be delivered by the nanoparticles of the invention. Exemplary agents to be delivered in accordance with the present invention include, but are not limited to, small molecules (e.g. cytotoxic agents), nucleic acids (e.g., siRNA, RNAi, and mircoRNA agents), proteins (e.g. antibodies), peptides, lipids, carbohydrates, hormones, metals, radioactive elements and compounds, drugs, vaccines, immunological agents, etc., and/or combinations thereof. In some embodiments, the agent to be delivered is an agent useful in the treatment of cancer (e.g., prostate cancer).

For instance, the targeting moiety may target or cause the particle to become localized at specific portions within a subject, and the payload may be delivered to those portions. In a particular embodiment, the drug or other payload may is released in a controlled release manner from the particle and allowed to interact locally with the particular targeting site (e.g., a tumor). The term "controlled release" (and variants of that term) as used herein (e.g., in the context of "controlled-release system") is generally meant to encompass release of a substance (e.g., a drug) at a selected site or otherwise controllable in rate, interval, and/or amount. Controlled release encompasses, but is not necessarily limited to, substantially continuous delivery, patterned delivery (e.g., intermittent delivery over a period of time that is interrupted by regular or irregular time intervals), and delivery of a bolus of a selected substance (e.g., as a predetermined, discrete amount if a substance over a relatively short period of time (e.g., a few seconds or minutes)).

For example, a targeting portion may cause the particles to become localized to a tumor, a disease site, a tissue, an organ, a type of cell, etc. within the body of a subject, depending on the targeting moiety used. For example, a low-molecular weight PSMA ligand may become localized to prostate cancer cells. The subject may be a human or non-human animal. Examples of subjects include, but are not limited to, a mammal such as a dog, a cat, a horse, a donkey, a rabbit, a cow, a pig, a sheep, a goat, a rat, a mouse, a guinea pig, a hamster, a primate, a human or the like.

In one set of embodiments, the payload is a drug or a combination of more than one drug. Such particles may be useful, for example, in embodiments where a targeting moiety may be used to direct a particle containing a drug to a particular localized location within a subject, e.g., to allow localized delivery of the drug to occur. Exemplary therapeutic agents include chemotherapeutic agents such as doxorubicin (adriamycin), gemcitabine (gemzar), daunorubicin, procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11, 10-hydroxy-7-ethylcamptothecin (SN38), dacarbazine, S-I capecitabine, ftorafur, 5'deoxyfluorouridine, UFT, eniluracil, deoxycytidine, 5-azacyto sine, 5-azadeoxycyto sine, allopurinol, 2-chloroadeno sine, trimetrexate, aminopterin, methylene-10-deazaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10,11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, and combinations thereof.

Non-limiting examples of potentially suitable drugs include anti-cancer agents, including, for example, docetaxel, mitoxantrone, and mitoxantrone hydrochloride. In another embodiment, the payload may be an anti-cancer drug such as 20-epi-1, 25 dihydroxyvitamin D3,4-ipomeanol, 5-ethynyluracil, 9-dihydrotaxol, abiraterone, acivicin, aclarubicin, acodazole hydrochloride, acronine, acylfiilvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisazuidinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caraceraide, carbetimer, carboplatin, carboxamide-amino-triazole, carboxyamidotriazole, carest M3, carmustine, earn 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethyhiorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocannycin SA, ebselen, ecomustine, edatrexate, edelfosine, edrecolomab, eflomithine, eflomithine hydrochloride, elemene, elsarnitrucin, emitefur, enloplatin, enpromate, epipropidine, epirubicin, epirubicin hydrochloride, episteride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ihnofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatm, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide, lobaplatin, lombricine, lometrexol, lometrexol sodium, lomustine, lonidamine, losoxantrone, losoxantrone hydrochloride, lovastatin, loxoribine, lurtotecan, lutetium texaphyrin lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C uihibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazorurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RH retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosafe sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride.

Once the inventive conjugates have been prepared, they may be combined with pharmaceutical acceptable carriers to form a pharmaceutical composition, according to another aspect of the invention. As would be appreciated by one of skill in this art, the carriers may be chosen based on the route of administration as described below, the location of the target issue, the drug being delivered, the time course of delivery of the drug, etc.

In one embodiment, the nanoparticles of this invention will contain nucleic acids such as siRNA.

Preferably, the siRNA molecule has a length from about 10-50 or more nucleotides. More preferably, the siRNA molecule has a length from about 15-45 nucleotides. Even more preferably, the siRNA molecule has a length from about 19-40 nucleotides. Even more preferably, the siRNA molecule has a length of from about 21-23 nucleotides.

The siRNA of the invention preferably mediates RNAi against a target mRNA. The siRNA molecule can be designed such that every residue is complementary to a residue in the target molecule. Alternatively, one or more substitutions can be made within the molecule to increase stability and/or enhance processing activity of said molecule. Substitutions can be made within the strand or can be made to residues at the ends of the strand.

The target mRNA cleavage reaction guided by siRNAs is sequence specific. In general, siRNA containing a nucleotide sequence identical to a portion of the target gene are preferred for inhibition. However, 100% sequence identity between the siRNA and the target gene is not required to practice the present invention. Sequence variations can be tolerated including those that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition.

Moreover, not all positions of an siRNA contribute equally to target recognition. Mismatches in the center of the siRNA are most critical and essentially abolish target RNA cleavage. In contrast, the 3' nucleotides of the siRNA do not contribute significantly to specificity of the target recognition. Generally, residues at the 3' end of the siRNA sequence which is complementary to the target RNA (e.g., the guide sequence) are not critical for target RNA cleavage.

Sequence identity may readily be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. NatL Acad Sci. USA 87:2264-68, modified as in Karlin and Altschul (1993) Proc. NatL Acad. Sci. USA 90:5873. Such an algorithm is incorporated into the BLAST programs (version 2.0) of Altschul, et al. (1990) J Mol Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 90% sequence identity, e.g., 91%, 92%, 93%, 94%, 95%, 96%, 97%, 98%, 99% or even 100% sequence identity, between the siRNA and the portion of the target mRNA is preferred. Alternatively, the siRNA may be defined functionally as a nucleotide sequence (or oligonucleotide sequence) that is capable of hybridizing with a portion of the target mRNA transcript (e.g., 400 mM NaCl, 40 mM PIPES pH 6.4, 1 mM EDTA, 50° C. or 70° C. hybridization for 12-16 hours; followed by washing). Additional hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6($\log_{10}$[Na+])+0.41 (% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference. The length of the identical nucleotide sequences may be at least about or about equal to 10, 12, 15, 17, 20, 22, 25, 27, 30, 32, 35, 37, 40, 42, 45, 47 or 50 bases.

In one embodiment, the siRNA molecules of the present invention are modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference. For example, the absence of a 2'hydroxyl may significantly enhance the nuclease resistance of the siRNAs in tissue culture medium.

In another embodiment of the present invention the siRNA molecule may contain at least one modified nucleotide analogue. The nucleotide analogues may be located at positions where the target-specific activity, e.g., the RNAi mediating activity is not substantially effected, e.g., in a region at the 5'-end and/or the 3'-end of the RNA molecule. Particularly, the ends may be stabilized by incorporating modified nucleotide analogues.

Nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar modified ribonucleotides, the 2'OH-group is replaced by a group selected from H, OR, R, halo, SH, SR, $NH_2$, NHR, $NR_2$ or $NO_2$, wherein R is C1-C6 alkyl, alkenyl or alkynyl and halo is F, Cl, Br or I.

Nucleotide analogues also include nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

RNA may be produced enzymatically or by partial/total organic synthesis, any modified ribonucleotide can be introduced by in vitro enzymatic or organic synthesis. In one embodiment, an siRNA is prepared chemically. Methods of synthesizing RNA molecules are known in the art, in particular, the chemical synthesis methods as described in Verina and Eckstein (1998), Annul Rev. Biochem. 67:99. In another embodiment, an siRNA is prepared enzymatically. For example, an siRNA can be prepared by enzymatic processing of a long, double-stranded RNA having sufficient complementarity to the desired target mRNA. Processing of long RNA can be accomplished in vitro, for example, using appropriate cellular lysates and siRNAs can be subsequently purified by gel electrophoresis or gel filtration. siRNA can then be denatured according to art-recognized methodologies. In an exemplary embodiment, siRNA can be purified from a mixture by extraction with a solvent or resin, precipitation, electrophoresis, chromatography, or a combination thereof. Alternatively, the siRNA may be used with no or a minimum of purification to avoid losses due to sample processing.

Alternatively, the siRNAs can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) Methods EnzynioL 180:51-62). The RNA may be dried for storage or dissolved in an aqueous solution. The solution may contain buffers or salts to inhibit annealing, and/or promote stabilization of the double strands.

Commercially available design tools and kits, such as those available from Ambion, Inc. (Austin, Tex.), and the Whitehead Institute of Biomedical Research at MIT (Cambridge, Mass.) allow for the design and production of siRNA. By way of example, a desired mRNA sequence can be entered into a sequence program that will generate sense and antisense target strand sequences. These sequences can then be entered into a program that determines the sense and antisense siRNA oligonucleotide templates. The programs can also be used to add, e.g., hairpin inserts or Ti promoter primer sequences. Kits also can then be employed to build siRNA expression cassettes.

In various embodiments, siRNAs are synthesized in vivo, in situ, and in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the siRNAs. Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses siRNAs from a recombinant construct may be produced by introducing the construct into a zygote, an embryonic stem cell, or another multipotent cell derived from the appropriate organism.

In one embodiment, the target mRNA of the invention specifies the amino acid sequence of at least one protein such as a cellular protein (e.g., a nuclear, cytoplasmic, transmembrane, or membrane-associated protein). In another embodiment, the target mRNA of the invention specifies the amino acid sequence of an extracellular protein (e.g., an extracellular matrix protein or secreted protein). As used herein, the phrase "specifies the amino acid sequence" of a protein means that the mRNA sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2. CBL, CSFIR, ERBA, ERBB, EBRB2, ERBB2, ERBB3, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES); tumor suppressor proteins (e.g., APC, BRCA1, BRCA2, MADH4, MCC, NF 1, NF2, RB 1, TP53, and WTI); and enzymes (e.g., ACC synthases and oxidases, ACP desaturases and hydroxylases, ADPglucose pyrophorylases, acetylases and deacetylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases), proteins involved in tumor growth (including vascularization) or in metastatic activity or potential, including cell surface receptors and ligands as well as secreted proteins, cell cycle regulatory, gene regulatory, and apoptosis regulatory proteins, immune response, inflammation, complement, or clotting regulatory proteins.

As used herein, the term "oncogene" refers to a gene which stimulates cell growth and, when its level of expression in the cell is reduced, the rate of cell growth is reduced or the cell becomes quiescent. In the context of the present invention, oncogenes include intracellular proteins, as well as extracellular growth factors which may stimulate cell proliferation through autocrine or paracrine function. Examples of human oncogenes against which siRNA and morpholino constructs can designed include c-myc, c-myb, mdm2, PKA-I (protein kinase A type I), Abl-1, Bcl2, Ras, c-Raf kinase, CDC25 phosphatases, cyclins, cyclin dependent kinases (cdks), telomerase, PDGF/sis, erb-B, fos, jun, mos, and src, to name but a few. In the context of the present invention, oncogenes also include a fusion gene resulted from chromosomal translocation, for example, the Bcr/Abl fusion oncogene.

Further proteins include cyclin dependent kinases, c-myb, c-myc, proliferating cell nuclear antigen (PCNA), transforming growth factor-beta (TGF-beta), and transcription factors nuclear factor kappaB (NF-.kappa.B), E2F, HER-2/neu, PKA, TGF-alpha, EGFR, TGF-beta, IGFIR, P12, MDM2, BRCA, Bcl-2, VEGF, MDR, ferritin, transferrin receptor, IRE, C-fos, HSP27, C-raf and metallothionein genes.

The siRNA employed in the present invention can be directed against the synthesis of one or more proteins. Additionally or alternatively, there can be more than one siRNA directed against a protein, e.g., duplicate siRNA or siRNA that correspond to overlapping or non-overlapping target sequences against the same target protein. Accordingly, in one embodiment two, three, four or any plurality of siRNAs against the same target mRNA can be included in the nanoparticles of the invention. Additionally, several siRNAs directed against several proteins can be employed. Alternatively, the siRNA can be directed against structural or regulatory RNA molecules that do not code for proteins.

In a preferred aspect of the invention, the target mRNA molecule of the invention specifies the amino acid sequence of a protein associated with a pathological condition. For example, the protein may be a pathogen-associated protein (e.g., a viral protein involved in immunosuppression or immunoavoidance of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. Alternatively, the protein may be a tumor-associated protein or an autoimmune disease-associated protein.

In one embodiment, the target mRNA molecule of the invention specifies the amino acid sequence of an endogenous protein (i.e. a protein present in the genome of a cell or organism). In another embodiment, the target mRNA molecule of the invention specifies the amino acid sequence of a heterologous protein expressed in a recombinant cell or a genetically altered organism. In another embodiment, the target mRNA molecule of the invention specifies the amino acid sequence of a protein encoded by a transgene (i.e., a gene construct inserted at an ectopic site in the genome of the cell). In yet another embodiment, the target mRNA molecule of the invention specifies the amino acid sequence of a protein encoded by a pathogen genome which is capable of infecting a cell or an organism from which the cell is derived.

By inhibiting the expression of such proteins, valuable information regarding the function of said proteins and therapeutic benefits which may be obtained from said inhibition may be obtained.

In one embodiment, the nanoparticles of this invention comprises one or more siRNA molecules to silence a PDGF beta gene, Erb-B gene, Src gene, CRK gene, GRB2 gene, RAS gene, MEKK gene, INK gene, RAF gene, Erk1/2 gene, PCNA(p21) gene, MYB gene, JIJN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, Skp2 gene, kinesin spindle protein gene, Bcr-Abl gene, Stat3 gene, cSrc gene, PKC gene, Bax gene, Bcl-2 gene, EGFR gene, VEGF gene, myc gene, NFKB gene, STAT3 gene, survivin gene, Her2/Neu gene, topoisomerase I gene, PLK1 gene, protein kinase 3 gene, CD31 gene, IGF-1 gene, topoisomerase II alpha gene, mutations in the p73 gene, mutations in the p21 (WAF 1/CIP 1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, mutations in the p53 tumor suppressor gene, mutations in the p53 family member DN-p63, mutations in the pRb tumor suppressor gene, mutations in the APC1 tumor suppressor gene, mutations in the BRCA1 tumor suppressor gene, mutations in the PTEN tumor suppressor gene, mLL fusiongene, BCRIABL fusion gene, TEL/AMLI fusion gene, EWS/FLI1 fusion gene, TLS/FUS1 fusion gene, PAX3/FKHR fusion gene, AML1/ETO fusion gene, alpha v-integrin gene, Flt-i receptor gene, tubulin gene, Human Papilloma Virus gene, a gene required for Human Papilloma Virus replication, Human Immunodeficiency Virus gene, a gene required for Human Immunodeficiency Virus replication, Hepatitis A Virus gene, a gene required for Hepatitis A Virus replication, Hepatitis B Virus gene, a gene required for Hepatitis B Virus replication, Hepatitis C Virus gene, a gene required for Hepatitis C Virus replication, Hepatitis D Virus gene, a gene required for Hepatitis D Virus replication, Hepatitis E Virus gene, a gene required for Hepatitis B Virus replication, Hepatitis F Virus gene, a gene required for Hepatitis F Virus replication, Hepatitis G Virus gene, a gene required for Hepatitis G Virus replication, Hepatitis H Virus gene, a gene required for Hepatitis H Virus replication, Respiratory Syncytial Virus gene, a gene that is required for Respiratory Syncytial Virus replication, Herpes Simplex Virus gene, a gene that is required for Herpes Simplex Virus replication, herpes Cytomegalovirus gene, a gene that is required for herpes Cytomegalovirus replication, herpes Epstein Barr Virus gene, a gene that is required for herpes Epstein Barr Virus replication, Kaposi's Sarcoma-associated Herpes Virus gene, a gene that is required for Kaposi's Sarcoma-associated Herpes Virus replication, JC Virus gene, human gene that is required for JC Virus replication, myxovirus gene, a gene that is required for myxovirus gene replication, rhinovirus gene, a gene that is required for rhinovirus replication, coronavirus gene, a gene that is required for coronavirus replication, West Nile Virus gene, a gene that is required for West Nile Virus replication, St. Louis Encephalitis gene, a gene that is required for St. Louis Encephalitis replication, Tick-borne encephalitis virus gene, a gene that is required for Tick-borne encephalitis virus replication, Murray Valley encephalitis virus gene, a gene that is required for Murray Valley encephalitis virus replication, dengue virus gene, a gene that is required for dengue virus gene replication, Simian Virus 40 gene, a gene that is required for Simian Virus 40 replication, Human T Cell Lymphotropic Virus gene, a gene that is required for Human T Cell Lymphotropic Virus replication, Moloney-Murine Leukemia Virus gene, a gene that is required for Moloney-Murine Leukemia Virus replication, encephalomyocarditis virus gene, a gene that is required for encephalomyocarditis virus replication, measles virus gene, a gene that is required for measles virus replication, Vericella zoster virus gene, a gene that is required for Vericella zoster virus replication, adenovirus gene, a gene that is required for adenovirus replication, yellow fever virus gene, a gene that is required for yellow fever virus replication, poliovirus gene, a gene that is required for poliovirus replication, poxvirus gene, a gene that is required for poxvirus replication, *plasmodium* gene, a gene that is required for *plasmodium* gene replication, *Mycobacterium ulcerans* gene, a gene that is required for *Mycobacterium ulcerans* replication, *Mycobacterium tuberculosis* gene, a gene that is required for *Mycobacterium tuberculosis* replication, *Mycobacterium leprae* gene, −185-a gene that is required for *Mycobacterium leprae* replication, *Staphylococcus aureus* gene, a gene that is required for *Staphylococcus aureus* replication, *Streptococcus pneumoniae* gene, a gene that is required for *Streptococcus pneumoniae* replication, *Streptococcus pyogenes* gene, a gene that is required for *Streptococcus pyogenes* replication, *Chiamydia pneumoniae* gene, a gene that is required for *Chiamydia pneumoniae* replication, *Mycoplasma pneumoniae* gene, a gene that is required for *Mycoplasma pneumoniae* replication, an integrin gene, a selectin gene, complement system gene, chemokine gene, chemokine receptor gene, GCSF gene, Gro1 gene, Gro2 gene, Gro3 gene, PF4 gene, MIG gene, Pro-Platelet Basic Protein gene, MIP-11 gene, MIP-1J gene, RANTES gene, MCP-1 gene, MCP-2 gene, MCP-3 gene, CMBKR1 gene, CMBKR2 gene, CMBKR3 gene, CMBKR5v, AIF-1 gene, 1-3 09 gene, a gene to a component of an ion channel, a gene to a neurotransmitter receptor, a gene to a neurotransmitter ligand, amyloid-family gene, presenilin gene, HD gene, DRPLA gene, SCA1 gene, SCA2 gene, MJD1 gene, CACNL1A4 gene, SCA7 gene, SCA8 gene, allele gene found in LOH cells, or one allele gene of a polymorphic gene. Examples of relevant siRNA molecules to silence genes and methods of making siRNA molecules can be found from commercial sources such as Dharmacon or from the following patent applications: US2005017667, WO2006066158, WO2006078278, U.S. Pat. No. 7,056,704, U.S. Pat. No. 7,078,196, U.S. Pat. No. 5,898,031, U.S. Pat. No. 6,107,094, EP 1144623, EU 1144623. While a number of specific gene silencing targets are listed, this list is merely illustrative and other siRNA molecules could also be used with the nanoparticles of this invention.

In one embodiment, the nanoparticles of this invention comprise an siRNA molecule having RNAi activity against an RNA, wherein the siRNA molecule comprises a sequence complementary to any RNA having coding or non-encoding sequence, such as those sequences referred to by GenBank Accession Nos. described in Table V of PCT/US03/05028 (International PCT Publication No. WO 03/4654) or otherwise known in the art.

In one embodiment, the nanoparticles of this invention comprise an siRNA molecule which silences the vascular endothelial growth factor gene. In another embodiment, the nanoparticles of this invention comprise an siRNA molecule which silences the vascular endothelial growth factor receptor gene.

In another embodiment, the nanoparticles of this invention comprise an siRNA molecule, wherein the sequence of the siRNA molecule is complementary to tumor-related targets, including, but not limited to, hypoxia-inducible factor-1 (HIF-1), which is found in human metastatic prostate PC3-M cancer cells (*Mol. Carcinog.* 2008 Jan. 31 [Epub ahead of print]); the HIF-1 downstream target gene (*Mol. Carcinog.* 2008 Jan. 31 [Epub ahead of print]), mitogen-activated protein kinases (MAPKs), hepatocyte growth factor (HGF), interleukin 12p70 (IL12), glucocorticoid-induced tumor necrosis factor receptor (GITR), intercellular adhesion molecule 1 (ICAM-1), neurotrophin-3 (NT-3), interleukin 17 (IL17), interleukin 18 binding protein a (IL18 Bpa) and epithelial-neutrophil activating peptide (ENA78) (see, e.g., "Cytokine profiling of prostatic fluid from cancerous prostate glands identifies cytokines associated with extent of tumor and inflammation", *The Prostate* Early view Published Online: 24 Mar. 2008); PSMA (see, e.g., "Cell-Surface labeling and internalization by a fluorescent inhibitor of prostate-specific membrane antigen" *The Prostate* Early view Published Online: 24 Mar. 2008); Androgen receptor (AR), keratin, epithelial membrane antigen, EGF receptor, and E cadherin (see, e.g., "Characterization of PacMetUT1, a recently isolated human prostate cancer cell line"); peroxisomes proliferators-activated receptor γ (PPARγ; see e.g., *The Prostate* Volume 68, Issue 6, Date: 1 May 2008, Pages: 588-598); the receptor for advanced glycation end products (RAGE) and the advanced glycation end products (AGE), (see, e.g., "V domain of RAGE interacts with AGEs on prostate carcinoma cells" *The Prostate* Early view Published Online: 26 Feb. 2008); the receptor tyrosine kinase erb-B2 (Her2/neu), hepatocyte growth factor receptor (Met), transforming growth factor-beta 1 receptor (TGFβR1), nuclear factor kappa B (NFκB), Jagged-1, Sonic hedgehog (Shh), Matrix metalloproteinases (MMPs, esp. MMP-7), Endothelin receptor type A ($ET_A$), Endothelin-1 (ET-1), Nuclear receptor subfamily 3, group C, member 1 (NR3C1), Nuclear receptor co-activator 1 (NCOA1), NCOA2, NCOA3, E1A binding protein p300 (EP300), CREB binding protein (CREBBP), Cyclin G associated kinase (GAK), Gelsolin (GSN), Aldo-keto reductase family 1, member C1 (AKR1C1), AKR1C2, AKR1C3, Neurotensin (NTS), Enolase 2(ENO2), Chromogranin B (CHGB, secretogranin 1), Secretagogin (SCGN, or EF-hand calcium binding protein), Dopa decarboxylase (DDC, or aromatic L-amino acid decarboxylase), steroid receptor co-activator-1 (SRC-1), SRC-2 (a.k.a. TIF2), SRC-3 (a.k.a. AIB-1) (see, e.g., "Longitudinal analysis of androgen deprivation of prostate cancer cells identifies pathways to androgen independence" *The Prostate* Early view Published Online: 26 Feb. 2008); estrogen receptors (ERα, ERβ or GPR30) (see, e.g., *The Prostate* Volume 68, Issue 5, Pages 508-516); the melanoma cell adhesion molecule (MCAM) (see, e.g., *The Prostate* Volume 68, Issue 4, Pages 418-426; angiogenic factors (such as vascular endothelial growth factor (VEGF) and erythropoietin), glucose transporters (such as GLUT1), BCL2/adenovirus E1B 19 kDa interacting protein 3 (BNIP3) (see, e.g., *The Prostate* Volume 68, Issue 3, Pages 336-343); types 1 and 2 5α-reductase (see, e.g., *The Journal of Urology* Volume 179, Issue 4, Pages 1235-1242); ERG and ETV1, prostate-specific antigen (PSA), prostate-specific membrane antigen (PSMA), prostate stem cell antigen (PSCA), α-Methylacyl coenzyme A racemase (AMACR), $PCA3^{DD3}$, glutathione-S-transferase, pi 1 (GSTP1), p16, ADP-ribosylation factor (ARF), O-6-methylguanine-DNA methyltransferase (MGMT), human telomerase reverse transcriptase (hTERT), early prostate cancer antigen (EPCA), human kallikrein 2 (HK2) and hepsin (see, e.g., *The Journal of Urology* Volume 178, Issue 6, Pages 2252-2259); bromodomain containing 2 (BRD2), eukaryotic translation initiation factor 4 gamma, 1 (eIF4G1), ribosomal protein L13a (RPL13a), and ribosomal protein L22 (RPL22) (see, e.g., *N Engl J Med* 353 (2005), p. 1224); HER2/neu, Derlin-1, ERBB2, AKT, cyclooxygenase-2 (COX-2), PSMD3, CRKRS, PERLD1, and C17ORF37, PPP4C, PARN, ATP6V0C, C16orf14, GBL, HAGH, ITFG3, MGC13114, MRPS34, NDUFB10, NMRAL1, NTHL1, NUBP2, POLR3K, RNPS1, STUB1, TBL3, and USP7. All of the references described herein are incorporated herein by reference in their entireties.

Thus, in one embodiment, the invention comprises a nanoparticle comprising a low molecular weight PSMA ligand, a biodegradable polymer, a stealth polymer, and an siRNA molecule. In one embodiment, the invention comprises a nanoparticle comprising a low molecular weight PSMA ligand, a biodegradable polymer, a stealth component, and an siRNA molecule that silences the vascular endothelial growth factor gene. In one embodiment, the invention comprises a nanoparticle comprising a low molecular weight PSMA ligand, a biodegradable polymer, a stealth component, and an siRNA molecule that silences the vascular endothelial growth factor receptor gene. In another embodiment, the invention comprises a nanoparticle comprising a low molecular weight PSMA ligand, PLGA, polyethylene glycol, and an siRNA molecule. In one embodiment, the invention comprises a nanoparticle comprising a low molecular weight PSMA ligand, a biodegradable polymer, a stealth component, and an siRNA molecule wherein the nanoparticle can selectively accumulate in the prostate or in the vascular endothelial tissue surrounding a cancer. In one embodiment, the invention comprises a nanoparticle comprising a low molecular weight PSMA ligand, a biodegradable polymer, a stealth component, and an siRNA molecule wherein the nanoparticle can selectively accumulate in the prostate or in the vascular endothelial tissue surrounding a cancer and wherein the nanoparticle can be endocytosed by a PSMA expressing cell.

In another embodiment, the siRNA that is incorporated into the nanoparticle of the invention are those that treat prostate cancer, such as those disclosed in U.S. application Ser. No. 11/021,159 (siRNA sequence is complementary to SEQ ID No.8: gaaggccagu uguauggac), and U.S. application Ser. No. 11/349,473 (discloses siRNAs that bind to a region from nucleotide 3023 to 3727 of SEQ ID No. 1). Both of these references are incorporated herein by reference in their entirety.

In another embodiment, the therapeutic agents of the nanoparticles of the invention include RNAs that can be used to treat cancer, such as anti-sense mRNAs and microRNAs. Examples of microRNAs that can be used as therapeutic agents for the treatment of cancer include those disclosed in Nature 435 (7043): 828-833; Nature 435 (7043): 839-843; and Nature 435 (7043): 834-838, all of which are incorporated herein by reference in their entireties.

Methods of Treatment

In some embodiments, targeted particles in accordance with the present invention may be used to treat, alleviate, ameliorate, relieve, delay onset of, inhibit progression of, reduce severity of, and/or reduce incidence of one or more symptoms or features of a disease, disorder, and/or condition. In some embodiments, inventive targeted particles may be used to treat cancer and/or cancer cells. In certain embodiments, inventive targeted particles may be used to treat any cancer wherein PSMA is expressed on the surface of cancer cells or in the tumor neovasculature in a subject in need thereof, including the neovasculature of prostate or non-prostate solid tumors. Examples of the PSMA-related indication include, but are not limited to, prostate cancer, non-small cell lung cancer, colorectal carcinoma, and glioblastoma.

The term "cancer" includes pre-malignant as well as malignant cancers. Cancers include, but are not limited to, prostate, gastric cancer, colorectal cancer, skin cancer, e.g., melanomas or basal cell carcinomas, lung cancer, cancers of the head and neck, bronchus cancer, pancreatic cancer, urinary bladder cancer, brain or central nervous system cancer, peripheral nervous system cancer, esophageal cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. "Cancer cells" can be in the form of a tumor, exist alone within a subject (e.g., leukemia cells), or be cell lines derived from a cancer.

Cancer can be associated with a variety of physical symptoms. Symptoms of cancer generally depend on the type and location of the tumor. For example, lung cancer can cause coughing, shortness of breath, and chest pain, while colon cancer often causes diarrhea, constipation, and blood in the stool. However, to give but a few examples, the following symptoms are often generally associated with many cancers: fever, chills, night sweats, cough, dyspnea, weight loss, loss of appetite, anorexia, nausea, vomiting, diarrhea, anemia, jaundice, hepatomegaly, hemoptysis, fatigue, malaise, cognitive dysfunction, depression, hormonal disturbances, neutropenia, pain, non-healing sores, enlarged lymph nodes, peripheral neuropathy, and sexual dysfunction.

In one aspect of the invention, a method for the treatment of cancer (e.g. prostate cancer) is provided. In some embodiments, the treatment of cancer comprises administering a therapeutically effective amount of inventive targeted particles to a subject in need thereof, in such amounts and for such time as is necessary to achieve the desired result. In certain embodiments of the present invention a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

In one aspect of the invention, a method for administering inventive compositions to a subject suffering from cancer (e.g. prostate cancer) is provided. In some embodiments, particles to a subject in such amounts and for such time as is necessary to achieve the desired result (i.e. treatment of cancer). In certain embodiments of the present invention a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

Inventive therapeutic protocols involve administering a therapeutically effective amount of an inventive targeted particle to a healthy individual (i.e., a subject who does not display any symptoms of cancer and/or who has not been diagnosed with cancer). For example, healthy individuals may be "immunized" with an inventive targeted particle prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with (e.g., within 48 hours, within 24 hours, or within 12 hours of) the onset of symptoms of cancer. Of course individuals known to have cancer may receive inventive treatment at any time.

In other embodiments, the nanoparticles of the present invention can be used to inhibit the growth of cancer cells, e.g., prostate cancer cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

Pharmaceutical Compositions

As used herein, the term "pharmaceutically acceptable carrier" means a non-toxic, inert solid, semi-solid or liquid filler, diluent, encapsulating material or formulation auxiliary of any type. Remington's Pharmaceutical Sciences. Ed. by Gennaro, Mack Publishing, Easton, Pa., 1995 discloses various carriers used in formulating pharmaceutical compositions and known techniques for the preparation thereof. Some examples of materials which can serve as pharmaceutically acceptable carriers include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN™ 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. If filtration or other terminal sterilization methods are not feasible, the formulations can be manufactured under aseptic conditions.

The pharmaceutical compositions of this invention can be administered to a patient by any means known in the art including oral and parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles of the present invention are administered to a subject in need thereof systemically, e.g., by IV infusion or injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be suppositories which can be prepared by mixing the inventive conjugate with suitable non-irritating excipients or carriers such as cocoa butter, polyethylene glycol, or a suppository wax which are solid at ambient temperature but liquid at body temperature and therefore melt in the rectum or vaginal cavity and release the inventive conjugate.

Dosage forms for topical or transdermal administration of an inventive pharmaceutical composition include ointments, pastes, creams, lotions, gels, powders, solutions, sprays, inhalants, or patches. The inventive conjugate is admixed under sterile conditions with a pharmaceutically acceptable carrier and any needed preservatives or buffers as may be required. Ophthalmic formulations, ear drops, and eye drops are also contemplated as being within the scope of this invention. The ointments, pastes, creams, and gels may contain, in addition to the inventive conjugates of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof. Transdermal patches have the added advantage of providing controlled delivery of a compound to the body. Such dosage forms can be made by dissolving or dispensing the inventive conjugates in a proper medium. Absorption enhancers can also be used to increase the flux of the compound across the skin. The rate can be controlled by either providing a rate controlling membrane or by dispersing the inventive conjugates in a polymer matrix or gel.

Powders and sprays can contain, in addition to the inventive conjugates of this invention, excipients such as lactose, talc, silicic acid, aluminum hydroxide, calcium silicates, and polyamide powder, or mixtures thereof. Sprays can additionally contain customary propellants such as chlorofluorohydrocarbons.

When administered orally, the inventive nanoparticles can be, but are not necessarily, encapsulated. A variety of suitable encapsulation systems are known in the art ("Microcapsules and Nanoparticles in Medicine and Pharmacy," Edited by Doubrow, M., CRC Press, Boca Raton, 1992; Mathiowitz and Langer J. Control. Release 5:13, 1987; Mathiowitz et al. Reactive Polymers 6:275, 1987; Mathiowitz et al. J. Appl. Polymer Sci. 35:755, 1988; Langer Ace. Chem. Res. 33:94, 2000; Langer J. Control. Release 62:7, 1999; Uhrich et al. Chem. Rev. 99:3181, 1999; Zhou et al. J. Control. Release 75:27, 2001; and Hanes et al. Pharm. Biotechnol. 6:389, 1995). The inventive conjugates may be encapsulated within biodegradable polymeric microspheres or liposomes. Examples of natural and synthetic polymers useful in the preparation of biodegradable microspheres include carbohydrates such as alginate, cellulose, polyhydroxyalkanoates, polyamides, polyphosphazenes, polypropylfumarates, polyethers, polyacetals, polycyanoacrylates, biodegradable polyurethanes, polycarbonates, polyanhydrides, polyhydroxyacids, poly(ortho esters), and other biodegradable polyesters. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides.

Pharmaceutical compositions for oral administration can be liquid or solid. Liquid dosage forms suitable for oral administration of inventive compositions include pharmaceutically acceptable emulsions, microemulsions, solutions, suspensions, syrups, and elixirs. In addition to an encapsulated or unencapsulated conjugate, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants, wetting agents, emulsifying and suspending agents, sweetening, flavoring, and perfuming agents. As used herein, the term "adjuvant" refers to any compound which is a nonspecific modulator of the immune response. In certain embodiments, the adjuvant stimulates the immune response. Any adjuvant may be used in accordance with the present invention. A large number of adjuvant compounds is known in the art (Allison Dev. Biol. Stand. 92:3-11, 1998; Unkeless et al. Annu. Rev. Immunol. 6:251-281, 1998; and Phillips et al. Vaccine 10:151-158, 1992).

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art.

It will be appreciated that the exact dosage of the PSMA-targeted particle is chosen by the individual physician in view of the patient to be treated, in general, dosage and administration are adjusted to provide an effective amount of the PSMA-targeted particle to the patient being treated. As used herein, the "effective amount" of an PSMA-targeted particle refers to the amount necessary to elicit the desired biological response. As will be appreciated by those of ordinary skill in this art, the effective amount of PSMA-targeted particle may vary depending on such factors as the desired biological endpoint, the drug to be delivered, the target tissue, the route of administration, etc. For example, the effective amount of PSMA-targeted particle containing an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

The nanoparticles of the invention may be formulated in dosage unit form for ease of administration and uniformity of dosage. The expression "dosage unit form" as used herein refers to a physically discrete unit of nanoparticle appropriate for the patient to be treated. It will be understood, however, that the total daily usage of the compositions of the present invention will be decided by the attending physician within the scope of sound medical judgment. For any nanoparticle, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of nanoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

The present invention also provides any of the above-mentioned compositions in kits, optionally with instructions for administering any of the compositions described herein by any suitable technique as previously described, for example, orally, intravenously, pump or implantable delivery device, or via another known route of drug delivery. "Instructions" can define a component of promotion, and typically involve written instructions on or associated with packaging of compositions of the invention. Instructions also can include any oral or electronic instructions provided in any manner. The "kit" typically defines a package including any one or a combination of the compositions of the invention and the instructions, but can also include the composition of the invention and instructions of any form that are provided in connection with the composition in a manner such that a clinical professional will clearly recognize that the instructions are to be associated with the specific composition.

The kits described herein may also contain one or more containers, which may contain the inventive composition and other ingredients as previously described. The kits also may contain instructions for mixing, diluting, and/or administrating the compositions of the invention in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the nanoparticle and the mode of use or administration. Suitable solvents for drug compositions are well known, for example as previously described, and are available in the literature. The solvent will depend on the nanoparticle and the mode of use or administration.

The invention also involves, in another aspect, promotion of the administration of any of the nanoparticle described herein. In some embodiments, one or more compositions of the invention are promoted for the prevention or treatment of various diseases such as those described herein via administration of any one of the compositions of the present invention. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention.

The following examples are intended to illustrate certain embodiments of the present invention, but do not exemplify the full scope of the invention.

EXAMPLES

The invention is further illustrated by the following examples. The examples should not be construed as further limiting.

Example 1

Synthesis of a Low-Molecular Weight PSMA Ligand (GL2)

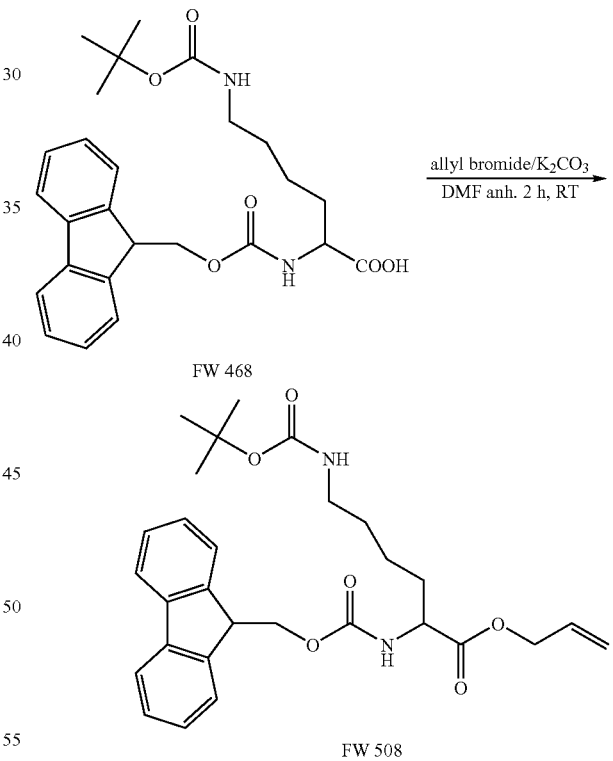

5 g (10.67 mmol) of the starting compound was dissolved in 150 mL of anhydrous DMF. To this solution was added allyl bromide (6.3 mL, 72 mmol) and $K_2CO_3$ (1.47 g, 10.67 mmol). The reaction was stirred for 2 h, the solvent was removed, the crude material was dissolved in AcOEt and washed with $H_2O$ until pH neutral. The organic phase was dried with $MgSO_4$ (anhydrous) and evaporated to give 5.15 g (95%) of material. (TLC in $CH_2Cl_2$:MeOH 20:1 Rf=0.9, started compound Rf=0.1, revealed with ninhydrin and uv light).

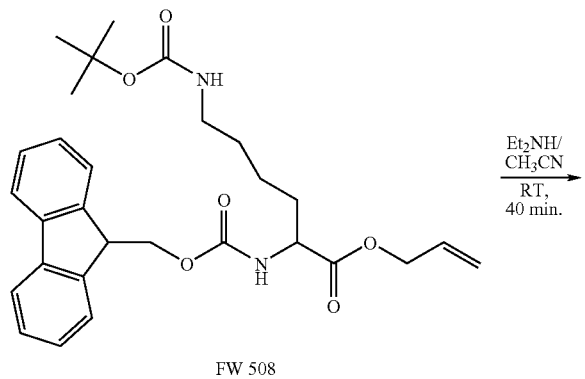

FW 508

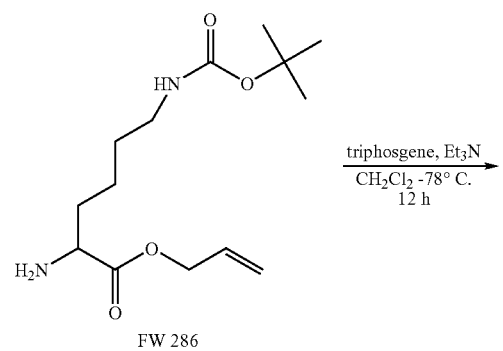

FW 286

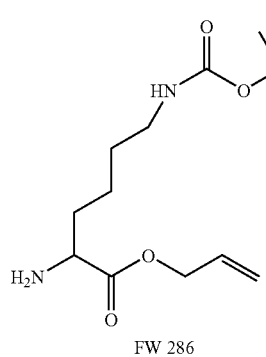

FW 286

To a solution of the compound (5.15 g, 10.13 mmol) in CH₃CN (50 mL) was added Et₂NH (20 mL, 0.19 mol). The reaction was stirred at room temperature for 40 min. The solvent was removed and the compound was purified by column chromatography (Hexane:AcOEt 3:2) to give 2.6 g (90%). (TLC in CH₂Cl₂:MeOH 10:1 Rf=0.4, revealed with ninhydrin (the compound has a violet color). ¹H-NMR (CDCl₃, 300 MHz) δ 5.95-5.85 (m, 1H, —CH₂CHCH₂), 5.36-5.24 (m, 2H, —CH₂CHCH₂), 4.62-4.60 (m, 3H, —CH₂CHCH₂, NHBoc), 3.46 (t, 1H, CH(Lys)), 3.11-3.07 (m, 2H, CH₂NHBoc), 1.79 (bs, 2H, NH₂), 1.79-1.43 (m, 6H, 3CH₂(Lys)), 1.43 (s, 9H, Boc).

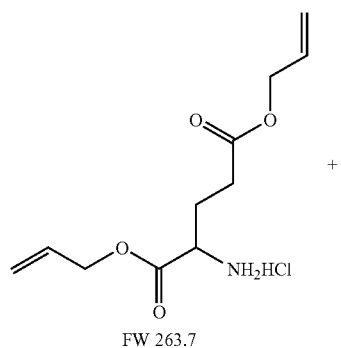

FW 263.7

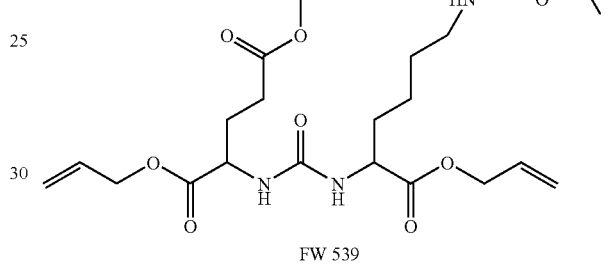

FW 539

To a stirred solution of diallyl glutamate (3.96 g, 15 mmol) and triphosgene (1.47 g, 4.95 mmol) in CH₂Cl₂ (143 mL) at −78° C. was added Et₃N (6.4 mL, 46 mmol) in CH₂Cl₂ (28 mL). The reaction mixture was allowed to warm to room temperature and stirred for 1.5 h. The Lysine derivative (2.6 g, 9.09 mmol) in a solution of CH₂Cl₂ (36 mL) was then added at −78° C. and the reaction was stirred at room temperature for 12 h. The solution was diluted with CH₂Cl₂, washed twice with H₂O, dried over MgSO₄ (anh.) and purified by column chromatography (Hexane:AcOEt 3:1→2:1→AcOEt) to give 4 g (82%) (TLC in CH₂Cl₂:MeOH 20:1 Rf=0.3, revealed with ninhydrin). ¹H-NMR (CDCl₃, 300 MHz) δ 5.97-5.84 (m, 3H, 3-CH₂CHCH₂), 5.50 (bt, 2H, 2NHurea), 5.36-5.20 (m, 6H, 3-CH₂CHCH₂), 4.81 (bs, 1H, NHBoc), 4.68-4.40 (m, 8H, 3-CH₂CHCH₂, CH(Lys), CH(glu)), 3.09-3.05 (m, 2H, CH₂NHBoc), 2.52-2.39 (m, 2H, CH₂(glu.)), 2.25-2.14 and 2.02-1.92 (2m, 2H, CH₂(glu.)), 1.87-1.64 (m, 4H, 2CH₂(Lys)), 1.51-1.35 (m, 2H, CH₂(Lys)), 1.44 (s, 9H, Boc).

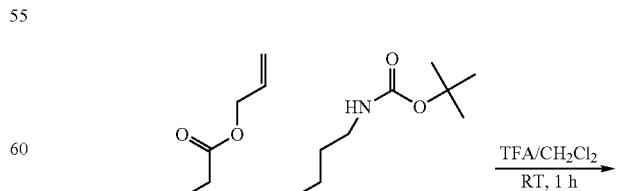

FW 539

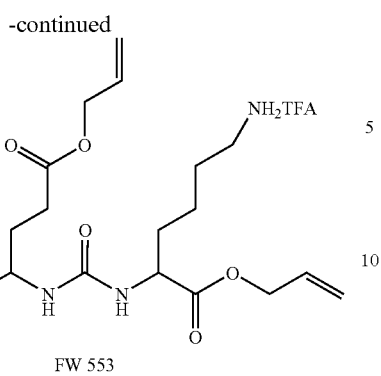

FW 553

To a solution of the compound (4 g, 7.42 mmol) in dry CH$_2$Cl$_2$ (40 mL) was added at 0° C. TFA (9 mL). The reaction was stirred at room temperature for 1 h. The solvent was removed under vacuum until complete dryness, to give 4.1 g (quantitative). (TLC in CH$_2$Cl$_2$:MeOH 20:1 Rf=0.1, revealed with ninhydrin). $^1$H-NMR (CDCl$_3$, 300 MHz) δ 6.27-6.16 (2d, 2H, 2NHurea), 5.96-5.82 (m, 3H, 3-CH$_2$CHCH$_2$), 5.35-5.20 (m, 6H, 3-CH$_2$CHCH$_2$), 4.61-4.55 (m, 6H, 3-CH$_2$CHCH$_2$), 4.46-4.41 (m, 2H, CH(Lys), CH(glu)), 2.99 (m, 2H, CH$_2$NHBoc), 2.46 (m, 2H, CH$_2$(glu.)), 2.23-2.11 and 2.01-1.88 (2m, 2H, CH$_2$(glu.)), 1.88-1.67 (m, 4H, 2CH$_2$(Lys)), 1.45 (m, 2H, CH$_2$(Lys)).

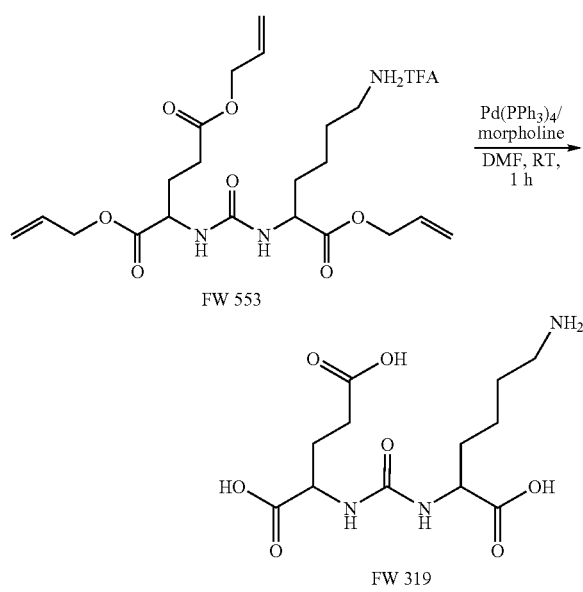

FW 553

FW 319

To a solution of the compound (2 g, 3.6 mmol) in DMF (anh.) (62 mL) under argon was added Pd(PPh$_3$)$_4$ (0.7 g, 0.6 mmol) and morpholine (5.4 mL, 60.7 mmol) at 0° C. The reaction was stirred at room temperature for 1 h. The solvent was removed. The crude product was washed twice with CH$_2$Cl$_2$, and then solved in H$_2$O. To this solution was added a diluted solution of NaOH (0.01 N) until the pH was very basic. The solvent was removed under reduced pressure. The solid was washed again with CH$_2$Cl$_2$, AcOEt, and a mixture of MeOH—CH$_2$Cl$_2$ (1:1), solved in H$_2$O and neutralized with Amberlite IR-120H$^+$ resin. The solvent was evaporated, and the compound was precipitated with MeOH, to give 1 g (87%) of GL2. $^1$H-NMR (D$_2$O, 300 MHz) δ 4.07 (m, 2H, CH(Lys), CH(glu)), 2.98 (m, 2H, CH$_2$NH$_2$), 2.36 (m, 2H, CH$_2$(glu.)), 2.08-2.00 (m, 1H, CH$_2$(glu)), 1.93-1.60 (m, 5H, CH$_2$(glu.), 2CH$_2$(Lys)), 1.41 (m, 2H, CH$_2$(Lys)). Mass ESI: 320.47 [M+H$^+$], 342.42 [M+Na$^+$].

Example 2

Synthesis of a Low-Molecular Weight PSMA Ligand (GL1)

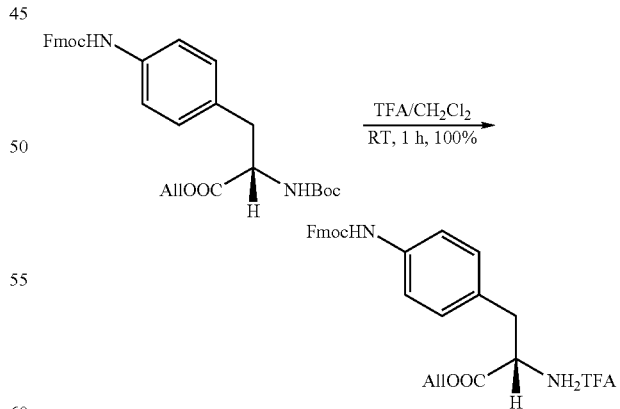

130 mg (0.258 mmol) of the starting compound was dissolved in 3 mL of DMF (anh.) To this solution was added allyl bromide (150 μL, 1.72 mmol) and K$_2$CO$_3$ (41 mg, 0.3 mmol). The reaction was stirred for 1 h, the solvent was removed, the crude product was dissolved in AcOEt and washed with H$_2$O until pH neutral. The organic phase was dried with MgSO$_4$ (anh.) and evaporated to give 130 mg (93%). (TLC in CH$_2$Cl$_2$:MeOH 20:1 Rf=0.9, started compound Rf=0.1, revealed with ninhydrin and uv light). $^1$H-NMR (CDCl$_3$, 300 MHz) δ 7.81-7.05 (12H, aromatics), 6.81 (bs, 1H, NHFmoc), 5.93-5.81 (m, 1H, —CH$_2$CHCH$_2$), 5.35-5.24 (m, 2H, —CH$_2$CHCH$_2$), 5.00 (bd, 1H, NHboc), 4.61-4.53 (m, 5H, —CH$_2$CHCH$_2$, CH$_2$(Fmoc), CH(pheala.)), 4.28 (t, 1H, CH(Fmoc)), 3.12-2.98 (m, 2H, CH$_2$(pheala.), 1.44 (s, 9H, Boc).

To a solution of the compound (120 mg, 0.221 mmol) in dry CH$_2$Cl$_2$ (2 mL) was added at 0° C. TFA (1 mL). The reaction was stirred at room temperature for 1 h. The solvent was removed under vacuum, water was added and removed again, CH$_2$Cl$_2$ was added and removed again until complete dryness to give 120 mg (quantitative). (TLC in CH$_2$Cl$_2$:

MeOH 20:1 Rf=0.1, revealed with ninhydrin and uv light). ¹H-NMR (CDCl₃, 300 MHz) δ 7.80-7.00 (13H, aromatics, NHFmoc), 5.90-5.75 (m, 1H, —CH₂CHCH₂), 5.35-5.19 (m, 3H, —CH₂CHCH₂, NHboc), 4.70-4.40 (2m, 5H, —CH₂CHCH₂, CH₂(Fmoc), CH(pheala.)), 4.20 (t, 1H, CH(Fmoc)), 3.40-3.05 (m, 2H, CH₂(pheala.)).

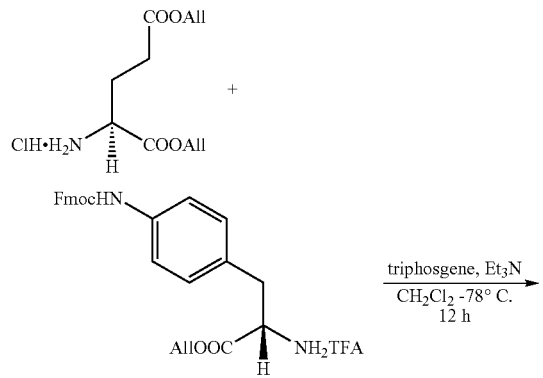

To a stirred solution of diallyl glutamate (110 mg, 0.42 mmol) and triphosgene (43 mg, 0.14 mmol) in CH₂Cl₂ (4 mL) at −78° C. was added Et₃N (180 μL, 1.3 mmol) in CH₂Cl₂ (0.8 mL). The reaction mixture was allowed to warm to room temperature and stirred for 1.5 h. The phenylalanine derivative (140 mg, 0.251 mmol) in a solution of CH₂Cl₂ (1 mL) and Et₃N (70 μL, 0.5 mmol) was then added at −78° C. and the reaction was stirred at room temperature for 12 h. The solution was diluted with CH₂Cl₂, washed twice with H₂O, dried over MgSO₄ (anh.) and purified by column chromatography (Hexane:AcOEt 3:1) to give 100 mg (57%) (TLC in CH₂Cl₂: MeOH 20:1 Rf=0.3, revealed with ninhydrin and uv light). ¹H-NMR (CDCl₃, 300 MHz) δ 7.80-6.95 (13H, aromatics, NHFmoc), 5.98-5.82 (m, 3H, 3-CH₂CHCH₂), 5.54 (bd, 1H, NHurea), 5.43-5.19 (m, 7H, 3-CH₂CHCH₂, NHurea), 4.85-4.78 (m, 1H, CH(pheala.)), 4.67-4.50 (m, 9H, 3-CH₂CHCH₂, CH₂(Fmoc), CH(glu.)), 4.28 (t, 1H, CH(Fmoc)), 3.05 (d, 2H, CH₂(pheala.)), 2.53-2.33 (m, 2H, CH₂(glu.)), 2.25-2.11 and 1.98-1.80 (2m, 2H, CH₂(glu.)).

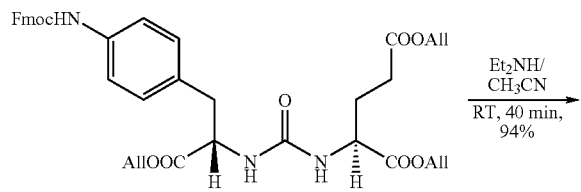

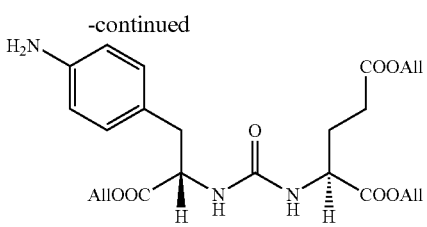

To a solution of the starting material (60 mg, 0.086 mmol) in CH₃CN (1 mL) was added Et₂NH (1 mL, 10 mmol). The reaction was stirred at room temperature for 40 min. The solvent was removed and the compound was purified by column chromatography (Hexane:AcOEt 2:1) to give 35 mg (85%). (TLC in CH₂Cl₂:MeOH 10:1 Rf=0.5, started compound Rf=0.75, revealed with ninhydrin (the compound has a violet color) and uv light). ¹H-NMR (CDCl₃, 300 MHz) δ 6.85 and 6.55 (2d, 4H, aromatics), 5.98-5.82 (m, 3H, 3-CH₂CHCH₂), 5.56 (bd, 1H, NHurea), 5.44-5.18 (m, 7H, 3-CH₂CHCH₂, NHurea), 4.79-4.72 (m, 1H, CH(pheala.)), 4.65-4.49 (m, 7H, 3-CH₂CHCH₂, CH(glu.)), 3.64 (bs, 2H, NH₂), 3.02-2.89 (m, 2H, CH₂(pheala.)), 2.49-2.31 (m, 2H, CH₂(glu.)), 2.20-2.09 and 1.91-1.78 (2m, 2H, CH₂(glu.)).

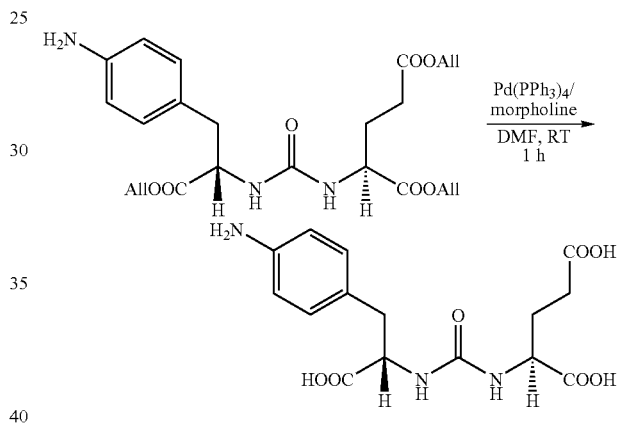

To a solution of the compound (50 mg, 0.105 mmol) in DMF (anh.; 1.5 mL) under argon was added Pd(PPh₃)₄ (21 mg, 0.018 mmol) and morpholine (154 μL, 1.77 mmol) at 0° C. The reaction was stirred at room temperature for 1 h. The solvent was removed. The crude material was washed with CH₂Cl₂ twice, and dissolved in H₂O. To this solution was added a diluted solution of NaOH (0.01 N) until the pH was very basic. The solvent was removed under reduced pressure. The solid was washed again with CH₂Cl₂, AcOEt, and mixture of MeOH—CH₂Cl₂ (1:1), solved in H₂O and neutralized with Amberlite IR-120H⁺ resin. The solvent was evaporated and the compound was precipitated with MeOH, to give 25 mg (67%) of GL1. ¹H-NMR (D₂O, 300 MHz) δ 7.08 and 6.79 (2d, 4H, aromatics), 4.21 (m, 1H, CH(pheala.)), 3.90 (m, 1H, CH(glu.)), 2.99 and 2.82 (2dd, 2H, CH₂(pheala.)), 2.22-2.11 (m, 2H, CH₂(glu.)), 2.05-1.70 (2m, 2H, CH₂(glu.)). ¹³C-NMR (D₂O, 75 MHz) δ 176.8, 174.5, 173.9 (3 COO), 153.3 (NHCONH), 138.8 (H₂N—C(Ph)), 124.5, 122.9, 110.9 (aromatics), 51.3 (CH(pheala.)), 49.8 (CH(glu.)), 31.8 (CH₂(pheala.)), 28.4 and 23.6 (2CH₂-glu.)). Mass ESI: 354.19 [M+H⁺], 376.23 [M+Na⁺].

Example 3

Nanoparticle Preparation

A non-limiting example of the preparation of the nanoparticles of the invention can be prepared using the synthesis procedure shown in FIG. 1B, wherein the ligand is, for example, GL1 or GL2. The urea-based PSMA inhibitor GL2, which has a free amino group located in a region not critical for PSMA binding, is synthesized from commercially available starting materials Boc-Phe(4NHFmoc)-OH and diallyl glutamic acid in accordance with the procedure shown in Scheme 1. The analog is attached to a PLGA-PEG diblock copolymer having a carboxyl group at the free terminus of the PEG using a standard conjugation chemistry, for example through use of water-soluble carbodiimide EDC and N-hydroxysuccinimide. Nanoparticles are formed using nanoprecipitation: The polymer ligand conjugate is dissolved in a water miscible organic solvent together with a drug other agent for tracking particle uptake. Additional non-functionalized polymer can be included to modulate the ligand surface density. The polymer solution is dispersed in an aqueous phase and the resulting particles are collected by filtration. The particles can be dried or immediately tested for cell uptake in vitro or anti-prostate tumor activity in vivo.

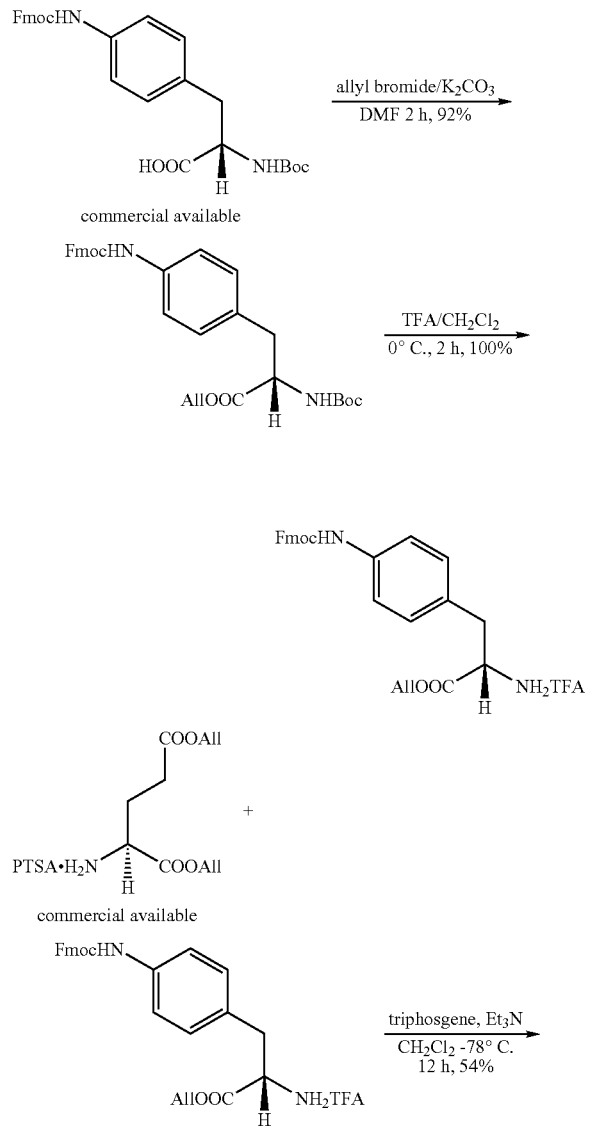

Scheme 1

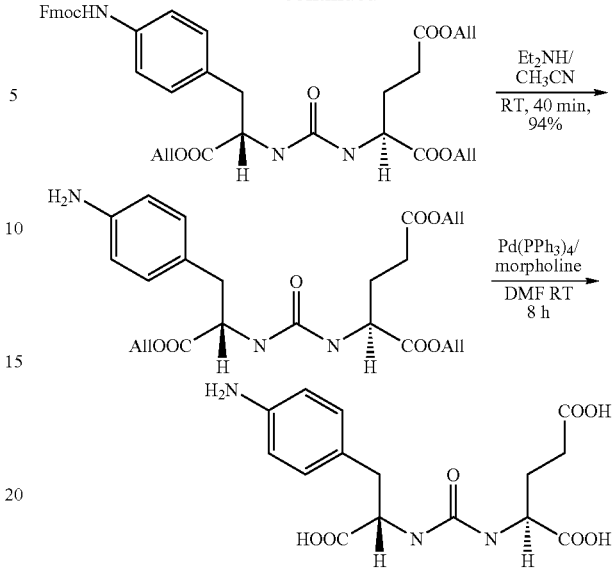

Using the procedure described above, a variety of target-specific stealth nanoparticles could be prepared, such as nanoparticles comprising PEG, PLA or PLGA, the chemotherapeutics described herein, and GL1 or GL2. Specific examples of the nanoparticles that could be prepared are shown in the table below:

| Therapeutic Agent | Biocompatible Polymer | Stealth Polymer | Targeting Moiety |
|---|---|---|---|
| mitoxantrone | PLGA | PEG | GL1 |
| mitoxantrone | PLA | PEG | GL1 |
| mitoxantrone | PGA | PEG | GL1 |
| mitoxantrone | PLGA | PEG | GL2 |
| mitoxantrone | PLA | PEG | GL2 |
| mitoxantrone | PGA | PEG | GL2 |
| mitoxantrone | PLGA | PEG-DSPE | GL1 |
| mitoxantrone | PLA | PEG-DSPE | GL1 |
| mitoxantrone | PGA | PEG-DSPE | GL1 |
| mitoxantrone | PLGA | PEG-DSPE | GL2 |
| mitoxantrone | PLA | PEG-DSPE | GL2 |
| mitoxantrone | PGA | PEG-DSPE | GL2 |
| docetaxel | PLGA | PEG | GL1 |
| docetaxel | PLA | PEG | GL1 |
| docetaxel | PGA | PEG | GL1 |
| docetaxel | PLGA | PEG | GL2 |
| docetaxel | PLA | PEG | GL2 |
| docetaxel | PGA | PEG | GL2 |
| docetaxel | PLGA | PEG-DSPE | GL1 |
| docetaxel | PLA | PEG-DSPE | GL1 |
| docetaxel | PGA | PEG-DSPE | GL1 |
| docetaxel | PLGA | PEG-DSPE | GL2 |
| docetaxel | PLA | PEG-DSPE | GL2 |
| docetaxel | PGA | PEG-DSPE | GL2 |
| doxorubicin | PLGA | PEG | GL1 |
| doxorubicin | PLA | PEG | GL1 |
| doxorubicin | PGA | PEG | GL1 |
| doxorubicin | PLGA | PEG | GL2 |
| doxorubicin | PLA | PEG | GL2 |
| doxorubicin | PGA | PEG | GL2 |
| doxorubicin | PLGA | PEG-DSPE | GL1 |
| doxorubicin | PLA | PEG-DSPE | GL1 |
| doxorubicin | PGA | PEG-DSPE | GL1 |
| doxorubicin | PLGA | PEG-DSPE | GL2 |
| doxorubicin | PLA | PEG-DSPE | GL2 |
| doxorubicin | PGA | PEG-DSPE | GL2 |
| gemcitabine | PLGA | PEG | GL1 |
| gemcitabine | PLA | PEG | GL1 |

-continued

| Therapeutic Agent | Biocompatible Polymer | Stealth Polymer | Targeting Moiety |
|---|---|---|---|
| gemcitabine | PGA | PEG | GL1 |
| gemcitabine | PLGA | PEG | GL2 |
| gemcitabine | PLA | PEG | GL2 |
| gemcitabine | PGA | PEG | GL2 |
| gemcitabine | PLGA | PEG-DSPE | GL1 |
| gemcitabine | PLA | PEG-DSPE | GL1 |
| gemcitabine | PGA | PEG-DSPE | GL1 |
| gemcitabine | PLGA | PEG-DSPE | GL2 |
| gemcitabine | PLA | PEG-DSPE | GL2 |
| gemcitabine | PGA | PEG-DSPE | GL2 |
| 5-fluorouracil | PLGA | PEG | GL1 |
| 5-fluorouracil | PLA | PEG | GL1 |
| 5-fluorouracil | PGA | PEG | GL1 |
| 5-fluorouracil | PLGA | PEG | GL2 |
| 5-fluorouracil | PLA | PEG | GL2 |
| 5-fluorouracil | PGA | PEG | GL2 |
| 5-fluorouracil | PLGA | PEG-DSPE | GL1 |
| 5-fluorouracil | PLA | PEG-DSPE | GL1 |
| 5-fluorouracil | PGA | PEG-DSPE | GL1 |
| 5-fluorouracil | PLGA | PEG-DSPE | GL2 |
| 5-fluorouracil | PLA | PEG-DSPE | GL2 |
| 5-fluorouracil | PGA | PEG-DSPE | GL2 |
| paclitaxel | PLGA | PEG | GL1 |
| paclitaxel | PLA | PEG | GL1 |
| paclitaxel | PGA | PEG | GL1 |
| paclitaxel | PLGA | PEG | GL2 |
| paclitaxel | PLA | PEG | GL2 |
| paclitaxel | PGA | PEG | GL2 |
| paclitaxel | PLGA | PEG-DSPE | GL1 |
| paclitaxel | PLA | PEG-DSPE | GL1 |
| paclitaxel | PGA | PEG-DSPE | GL1 |
| paclitaxel | PLGA | PEG-DSPE | GL2 |
| paclitaxel | PLA | PEG-DSPE | GL2 |
| paclitaxel | PGA | PEG-DSPE | GL2 |
| daunorubicin | PLGA | PEG | GL1 |
| daunorubicin | PLA | PEG | GL1 |
| daunorubicin | PGA | PEG | GL1 |
| daunorubicin | PLGA | PEG | GL2 |
| daunorubicin | PLA | PEG | GL2 |
| daunorubicin | PGA | PEG | GL2 |
| daunorubicin | PLGA | PEG-DSPE | GL1 |
| daunorubicin | PLA | PEG-DSPE | GL1 |
| daunorubicin | PGA | PEG-DSPE | GL1 |
| daunorubicin | PLGA | PEG-DSPE | GL2 |
| daunorubicin | PLA | PEG-DSPE | GL2 |
| daunorubicin | PGA | PEG-DSPE | GL2 |

Example 4

Small Molecule Targeting Moiety Mediated Binding/Uptake of Nano-Particles in LNcap Cells The binding and uptake of nanoparticles (NP-GL1, NP-GL2) with surface bound ligands GL1 (based on Glutamic Acid/4-Amino-phenylalanine) and GL2 (based on Glutamic Acid/Lysine) by high PSMA expressing LNCap cells was tested by comparison with bare PLGA-PEG nano-particles (NP) as negative control and amine-terminated A10 prostate-specific membrane antigen (PSMA) aptamer (Apt)-bearing NP's (NP-Apt) as positive control. NP-GL1, NP-GL2, NP, and NP-Apt uptake by LNCap cells and low PSMA expressing PC3 cells were compared to evaluate specific PSMA mediated binding/uptake of the NP-GL1, NP-GL2.

Materials:

Diblock copolymer $PLGA_{0.67}$-$PEG_{5000}$-$CO_2H$ (50 mg/ml stock solution in ACN); Aptamer (1 mg/mL); Glutamic acid/Phenyl Alanine based Ligand (GL1); Glutamic acid/Lysine based Ligand (GL2); EDC. HCl (Pierce Biotech); SulfoNHS (Pierce Biotech), Phosphate Buffered Saline, PBS (Sigma); Fixation buffer: freshly prepared 4% formaldehyde in PBS; Blocking solution: freshly prepared 1% BSA in PBS; Blocking and permeabilization solution: freshly prepared 0.1 Triton X100 in blocking solution. Alexa-568 phalloidin (5 U/mL), NBD Cholesterol (Invitrogen); DAPI (Sigma): 0.1 mg/mL; Vectashield (Vector Labs); Nail polish.

Nanoparticle Preparation:

Nanoparticles based on PLGA-PEG-$CO_2H$ diblock copolymers were prepared by the nano-precipitation method. GL1, GL2 and Apt were covalently bound to the carboxylic acid terminus of the nano-particle PEG corona in aqueous PBS suspension. Covalent conjugation of GL1, GL2 and Apt to NP's was based on EDC/NHS activation of the carboxylic acid PEG terminus and subsequent reaction of the active succinimide ester end groups with the amine functionality on GL1, GL2 and Apt using the following procedure:

PLGA-PEG-$CO_2H$ stock solution (1.2 mL, 50 mg/mL solution in acetonitrile) was diluted with acetonitrile to yield 6 ml of 10 mg/mL diblock solution. NBD Cholesterol (600 uL, 1 mg/mL solution in DMF) was added to the above diblock solution and the mixture added drop wise to 12 mL of stirred De-ionized water (18 MΩ). The resulting NP suspension was allowed to stir (400 rpm) open in a fume hood for 2 hr and subsequently purified by ultra-filtration using re-generated cellulose based Amicon Filters (MWCO 5000 Da) to remove residual acetonitrile, DMF and un-encapsulated NBD as follows. NP suspension (16 mL) was transferred in four equal portions to four 15 mL Amicon Centrifugal Filtration tubes and concentrated to 250-400 uL each (5000 g×10 minutes). The concentrated suspensions were diluted with DI water (3 mL) and similarly concentrated (200-300 uL each) prior to being reconstituted into Sterile PBS (1.5 mL each).

The resulting four 10 mg/mL NP suspensions were subsequently treated as follows:

NP formulation with no targeting surface bound Ligand (NP, 10 mg/mL NP suspension) was used from above with no further treatment. 100 uL per well NP was used in the cell uptake study.

NP-GL1 and NP-GL2 formulations were prepared by activation of the carboxylic acid terminus of the PEG corona using a 1 mL sterile PBS solution of EDC/NHS (1.9 mg/mL, 2.2 mg/mL, 20 equivalent w.r.t. $CO_2H$) for 15 minutes at room temperature and subsequent coupling to GL1 and GL1 (1 mL sterile PBS solutions, 3.5 mg/mL and 3.1 mg/mL, respectively) after quenching (3 minutes) un-reacted EDC using 2-mercaptoethanol (2.8 uL, 4 equivalents w.r.t. EDC). NP-GL1 and NP-GL2 were concentrated 14 fold by ultra-filtration and subsequently re-constituted into sterile PBS each (9 mg/mL NP suspension). 100 uL per well NP-GL1 and NP-GL2 were used in the cell uptake study.

NP-Apt formulation was prepared by a one-pot EDC/NHS activation (75 mg/45 mg, 200 equivalents w.r.t. $CO_2H$) and Apt coupling (150 ug Apt) followed by purification by 15 fold concentration and re-dispersion in DI H2O (thrice) using ultra-filtration in Amicon Centrifuge Filters (MWCO 5000 Da). The final concentrate was reconstituted into 1.6 mL sterile PBS (9 mg/mL NP suspension) and 100 uL per well NP-Apt was used in the cell uptake study.

NP Uptake and Staining:

Day 0

Plated ~30,000 cells/well on 8 well chamber slides. If cells looked healthy after 8-16 hrs, NP binding and uptake protocol was conducted. If not, the cells were incubated longer (~24 h total) allowing them to adhere and spread; the monolayer should be ~50% confluent.

Day 1
Side Design: 4 Conditions.

Slide 1: LNCaP

| Vacant | GL1-NP | NP | Apt-NP | NP on LNCaP |
|---|---|---|---|---|
| Vacant | GL1-NP | NP | Apt-NP | |

Slide 2: PC3

| Vacant | GL1-NP | NP | Apt-NP | NP on PC3 |
|---|---|---|---|---|
| Vacant | GL1-NP | NP | Apt-NP | |

Media in all wells was replaced with 300 µl of fresh media supplemented with 10% FBS per well. 100 µL per well of NP solution (500 µg NP per well) in PBS was added. Slides were incubated for 30 min at 37° C. and washed 3× gently with PBS. The cells were fixed with freshly made fixation buffer for 30 min at RT, then washed gently with PBS 2×1 min. Cells were incubated with the blocking/permeabilization buffer for 1 hr at RT. Cells were then stained with Alexa-Fluor 568 Phalloidin in the blocking/permeabilization buffer at RT for 1 hr and washed with PBS 3×5 min with gentle shaking. 100 µL DAPI (0.1 mg/mL) per well was added and incubated for 15 minutes at RT and washed 3× with PBS. 1 drop of Vectashield per well was added and slides were mounted with a glass cover slip. The cover slip was sealed with clear nail polish.

Figure 4:
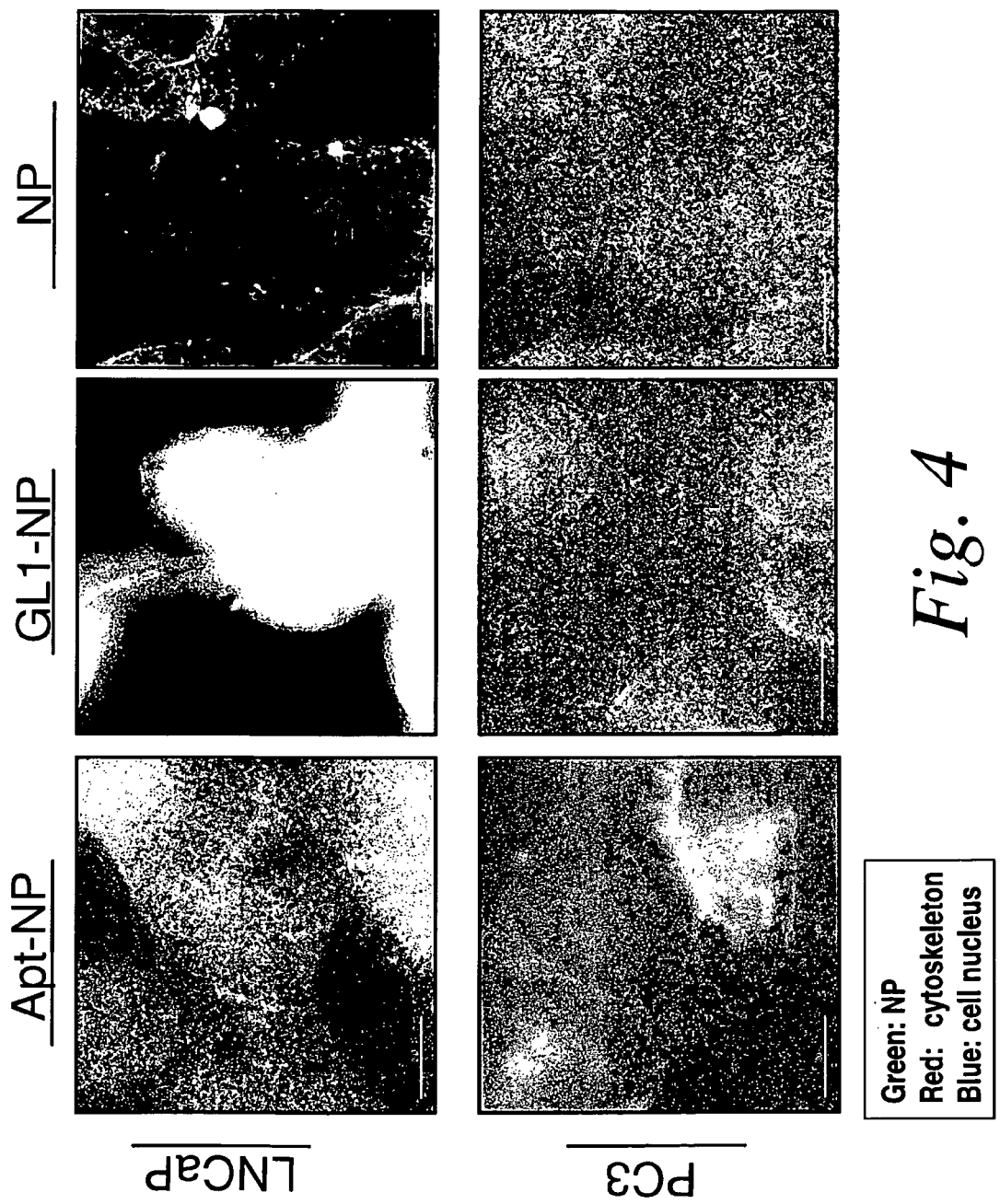
FIG. 4 demonstrates cell uptake of the nanoparticles of the invention.

Samples were kept protected from light in the refrigerator.
Microscopy:

Slides were imaged using an inverted Leica microscope, equipped with a 60× oil-immersion objective. Intensity set at 10% for NBD and Alexa, and 1% for DAPI. Exposure times were 0.05 sec for DAPI, 1 sec for NBD and 0.5 sec for Alexa. Images were taken at 0.5 um increments for 70 sections along the z axis. All images were then merged and deconvolved using Softworx.
Image Analysis:

After processing, the images shown in FIG. 4 were obtained. These images show the differences between the experimental conditions. The green color shows the location of the nanoparticles, the red stains the actin in the cytoskeleton and the blue stain shows the nucleus. The prevalence of the green stain in the NP-GL1-LNCaP well indicates that the GL is effective in binding to PSMA and that NP-GL1 nanoparticles are readily being taken up by the cells. The lack of significant green staining in the NP wells indicates that the particles are not being non-specifically endocytosed by the cells.

Example 5

Amphiphilic Layer Encapsulated Target Specific Nanoparticle

An amphiphilic layer encapsulated target specific nanoparticle can be prepared using the following procedure. As noted above, the amphiphilic layer can reduce water penetration into the nanoparticle, thereby enhancing drug encapsulation efficiency and slowing drug release.
1) Amphiphilic Layer: Weigh out 10 mg lecithin soybean (MP Biomedicals, LLC: 1-800-854-0530, www.mpbio.com) in a glovebox in a 20 mL scintillation vial and dissolve in 10 mL $H_2O$+4% EtOH to get a 1 mg/ml solution.
2) Non fluorescent Polymer: Weigh out 6 mg_PLGA-Ester terminal Polymer [DURECT Corporation (205)-620-0025, LACTEL® Absorbable Polymers; 50:50 Poly(DL-lactide-co-glycolide), Ester Terminal; Inherent Viscosity Range: 0.76-0.94 dL/g in HFIP; Store at $\leq-10°$ C. as crystals. Moisture sensitive. Open after bottle has warmed up] in a glovebox into 7 mL scintillation vial. Add 0.6 mL ACN for final conc of 10 mg/mL. Vortex to mix.
3) DSPE-PEG-OME: Weigh out 10 mg of PEG [Avanti® Polar Lipids, Inc.; www.avantilipids.com; 1,2-Distearoyl-sn-Glycero-3-Phosphoethanolamine-N-[methoxy(Polyethylene Glycol)2000] (Ammonium Salt) 880120P; MW: 2805.54] is weighed out in a glovebox into a 10 mL scintillation vial. Add 10 mL 4% EtOH DI H2O for final concentration of 1 mg/mL. Vortex to mix.

Protocol (Make 5 mg Batches at 5 mg/ml PLGA) Per NP Batch:
1) Lipid mixture: prepare each in 7 mL scintillation vial
   a) Lipid solution:

| Lecithin (1 mg/ml) | 0.35 mg or 0.35 mL |
| DSPE-PEG (1 mg/ml) or DSPE-PEG-GL2 | 0.15 mg or 0.15 mL |
| $H_2O$ + 4% ethanol | 1.5 mL |

2) Add stir-bar and stir;
3) PLGA solutions: aliquot in 7 mL scintillation vials;
   b) PLGA solution:

| PLGA | 0.5 mL |
| ACN | 0.5 mL | a. Vortex;
4) Heat lipid mixture at 68° C. for ~3-4 min;
5) Add PLGA drop-wise while heating lipids;
6) Vortex for 3 min;
7) Add 1 mL DI $H_2O$ drop-wise, stirring. (total volume: 4 mL);
8) Stir for 2 h with cap open at room temperature;
9) Transfer to dialysis cassette (PIERCE Slide-A-Lyzer 10K MWCO Dialysis Cassettes) for 3 h in 1000-fold $H_2O$;
10) Change dialysis buffer at 1 hour, 2 hour, and 3 hours;
11) During dialysis, prepare 5 vol % Tween 80 buffer (100 mL) for freezing nanoparticle with 0.5 vol % Tween 80;
12) Prepare/label Amicon tubes;
13) After dialysis, remove aliquot (1.0 mg) for size and zeta potential measurements;
14) Use Amicon filter (Amicon®Ultra-15 Ultracel 10K Cat #: UFC8 010 96) to spin ~3× at 4000 rpm for 10 min to concentrate to 1 ml, topping off with PBS;
15) Remove 1.0 mg aliquot from each batch and measure size and zeta potential;
16) Aliquot 3.0 mg of each batch into eppendorf tubes;
17) Add Tween to 0.5 vol % into epp tubes for each batch;
18) Flash freeze tubes in liquid N2 and place in freezer.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

The invention claimed is:

1. A stealth nanoparticle having a diameter of 80 nm to 200 nm, comprising a diblock copolymer of poly (ethylene glycol) and poly (lactic) acid (PLA) or poly (ethylene glycol) and poly (lactic acid-co-glycolic) acid (PLGA);

a prostate specific membrane antigen ligand conjugate comprising by:

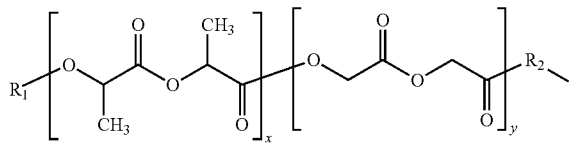

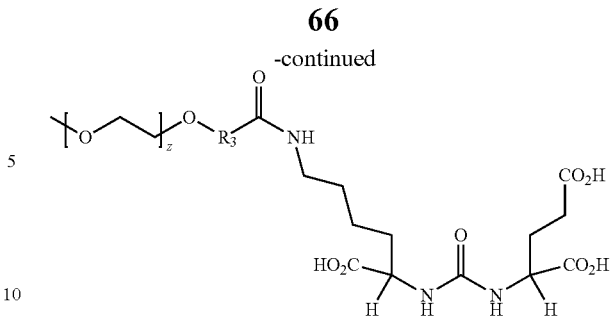

wherein $R_1$ and $R_3$ are alkyl groups, $R_2$ is an ester or amide linkage, $x+y=20$ to 1720, and $z=25$ to 455; and a therapeutic agent wherein the nanoparticle comprises an amount of the prostate specific membrane antigen ligand conjugate that is effective for the treatment of solid tumors expressing prostate specific membrane antigen in the tumor neovasculature when the nanoparticle is intravenously administered to the patient in need thereof.

2. The nanoparticle of claim 1, wherein the nanoparticle further comprises a polymer selected from the group consisting of PLGA or PLA.

3. The nanoparticle of claim 1, wherein the therapeutic agent is docetaxel.

4. The nanoparticle of claim 1, wherein y is 0.

\* \* \* \* \*